United States Patent
Whittingham et al.

(10) Patent No.: US 12,202,821 B2
(45) Date of Patent: Jan. 21, 2025

(54) HERBICIDAL COMPOUNDS

(71) Applicant: SYNGENTA CROP PROTECTION AG, Basel (CH)

(72) Inventors: William Guy Whittingham, Bracknell (GB); John Williams, Bracknell (GB); Christopher John Mathews, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 659 days.

(21) Appl. No.: 17/613,290

(22) PCT Filed: May 21, 2020

(86) PCT No.: PCT/EP2020/064212
§ 371 (c)(1),
(2) Date: Nov. 22, 2021

(87) PCT Pub. No.: WO2020/239607
PCT Pub. Date: Dec. 3, 2020

(65) Prior Publication Data
US 2022/0227744 A1     Jul. 21, 2022

(30) Foreign Application Priority Data

May 29, 2019  (GB) .................................. 1907602
Oct. 3, 2019  (GB) .................................. 1914260
Feb. 18, 2020  (GB) .................................. 2002209

(51) Int. Cl.
| C07D 413/10 | (2006.01) |
| A01N 43/80 | (2006.01) |
| A01P 13/00 | (2006.01) |
| C07D 413/14 | (2006.01) |

(52) U.S. Cl.
CPC ........... *C07D 413/10* (2013.01); *A01N 43/80* (2013.01); *A01P 13/00* (2021.08); *C07D 413/14* (2013.01)

(58) Field of Classification Search
CPC ..... C07D 413/10; C07D 413/14; A01P 13/10; A01N 43/80
See application file for complete search history.

(56) References Cited

U.S. PATENT DOCUMENTS

| 5,726,126 A * | 3/1998 | Crews, Jr. ............ C07D 251/30 |
| | | 504/225 |
| 6,602,825 B1 | 8/2003 | Menke et al. |
| 10,550,111 B2 | 2/2020 | Liu et al. |
| 2018/0230139 A1 | 8/2018 | Liu et al. |

FOREIGN PATENT DOCUMENTS

| CN | 1138580 A | 12/1996 |
| CN | 1341105 A | 3/2002 |
| CN | 105753853 A | 7/2016 |
| CN | 108207997 A | 6/2018 |
| CN | 108570041 A | 9/2018 |
| EP | 0 745 595 A1 | 12/1996 |
| EP | 0745599 A2 | 12/1996 |
| JP | 9-25270 A | 1/1997 |
| JP | 9-132569 A | 5/1997 |
| JP | 2016060717 A | 4/2016 |
| WO | 0008000 A1 | 2/2000 |

OTHER PUBLICATIONS

GB Search Report for GB patent application GB1907602.5, mailed Oct. 29, 2019.
Wang, Da-Wei et al., Discovery of Novel N-Isoxazolinylphenyltriazinones as Promising Protoporphyrinogen IX Oxidase Inhibitors, Journal of Agricultural and Food Chemistry, Oct. 21, 2019, vol. 67, No. 45, pp. 12382-12392.
Written Opinion of the International Searching Authority and International Search Report for International Patent Application PCT/EP2020/064212, mailed Jul. 2, 2020.

* cited by examiner

*Primary Examiner* — Timothy R Rozof
(74) *Attorney, Agent, or Firm* — BakerHostetler; Toni-Junell Herbert

(57) ABSTRACT

Compounds of the formula (I) wherein the substituents are as defined in claim 1, useful as a pesticides, especially as herbicides.

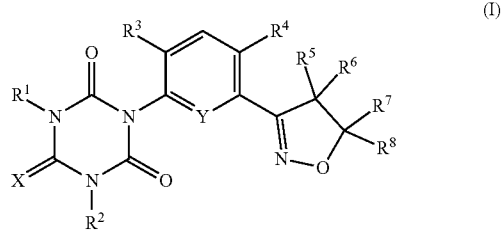

19 Claims, No Drawings

HERBICIDAL COMPOUNDS

CROSS-REFERENCE TO RELATED APPLICATIONS

This application is a 371 National Stage application of International Application No. PCT/EP2020/064212 filed May 21, 2020, which claims priority to GB 1907602.5, filed May 29, 2019, GB 1914260.3, filed Oct. 3, 2019, and GB 2002209.1, filed Feb. 18, 2020, the entire contents of these applications are hereby incorporated by reference.

The present invention relates to herbicidally active isoxazoline derivatives, as well as to processes and intermediates used for the preparation of such derivatives. The invention further extends to herbicidal compositions comprising such derivatives, as well as to the use of such compounds and compositions for controlling undesirable plant growth: in particular the use for controlling weeds, in crops of useful plants.

The present invention is based on the finding that isoxazoline derivatives of formula (I) as defined herein, exhibit surprisingly good herbicidal activity. Thus, according to the present invention there is provided a compound of formula (I) or an agronomically acceptable salt thereof:

wherein

X is selected from the group consisting of oxygen and sulfur;

Y is selected from the group consisting of C—H and nitrogen;

$R^1$ is selected from the group consisting of hydrogen and $C_1$-$C_6$alkyl;

$R^2$ is selected from the group consisting of hydrogen, amino, $C_1$-$C_6$alkyl, $C_3$-$C_6$alkenyl and $C_3$-$C_6$alkynyl;

$R^3$ is selected from the group consisting of hydrogen, halogen, $C_1$-$C_4$alkyl, $C_1$-$C_4$haloalkyl, $C_1$-$C_4$alkoxy, $C_1$-$C_4$haloalkoxy and $C_1$-$C_4$alkylsulfonyl;

$R^4$ is selected from the group consisting of hydrogen, halogen, cyano, aminocarbonyl, aminothiocarbonyl, $C_1$-$C_4$alkyl, $C_1$-$C_4$haloalkyl, $C_1$-$C_4$alkoxy, $C_1$-$C_4$haloalkoxy and $C_1$-$C_4$alkylsulfonyl;

each $R^5$ and $R^6$ is independently selected from the group consisting of hydrogen, cyano, $C_1$-$C_6$alkyl, $C_1$-$C_6$haloalkyl, $C_1$-$C_4$alkylsulfonyl, $CO_2R^9$, $CONR^{10}R^{11}$ and $CH_2OR^{12}$;

each $R^7$ and $R^8$ is independently selected from the group consisting of hydrogen, cyano, $C_1$-$C_6$alkyl, $C_1$-$C_6$haloalkyl, $C_1$-$C_4$alkoxy, $C_1$-$C_4$alkylsulfonyl, $C(=Z)R^{15}$, $CO_2R^9$, $CONR^{10}R^{11}$ and $CH_2OR^{12}$;

Z is selected from the group consisting of oxygen, $NOR^{16}$ and $NN(R^{16})_2$;

$R^9$ is selected from the group consisting of hydrogen, $C_1$-$C_{10}$alkyl, $C_1$-$C_{10}$haloalkyl, $C_3$-$C_6$alkenyl, $C_3$-$C_6$haloalkenyl, $C_3$-$C_6$alkynyl, $C_1$-$C_4$alkoxy$C_1$-$C_6$alkyl, $C_1$-$C_4$haloalkoxy$C_1$-$C_6$alkyl, $C_6$-$C_{10}$aryl$C_1$-$C_3$alkyl, $C_6$-$C_{10}$aryl$C_1$-$C_3$alkyl substituted by 1-4 groups $R^{13}$, heteroaryl$C_1$-$C_3$alkyl and heteroaryl$C_1$-$C_3$alkyl substituted by 1-3 groups $R^{13}$;

$R^{10}$ is selected from the group consisting of hydrogen, $C_1$-$C_6$alkyl and $SO_2R^{14}$;

$R^{11}$ is selected from the group consisting of hydrogen and $C_1$-$C_6$alkyl; or $R^{10}$ and $R^{11}$ together with the nitrogen to which they are attached form a 3- to 6-membered heterocyclyl ring, which optionally contains an oxygen atom;

$R^{12}$ is selected from the group consisting of hydrogen, $C_1$-$C_4$alkyl, $C_1$-$C_4$haloalkyl, $C_1$-$C_4$alkylsulfonyl, $C_1$-$C_4$haloalkylsulfonyl, phenylsulphonyl, phenylsulfonyl substituted by 1-2 groups $R^{13}$; $C_1$-$C_4$alkylcarbonyl, $C_1$-$C_4$haloalkylcarbonyl, $C_6$-$C_{10}$arylcarbonyl, $C_6$-$C_{10}$arylcarbonyl substituted by 1-4 groups $R^{13}$, heteroarylcarbonyl, heteroarylcarbonyl substituted by 1-3 groups $R^{13}$, $C_6$-$C_{10}$aryl$C_1$-$C_3$alkylcarbonyl, $C_6$-$C_{10}$aryl$C_1$-$C_3$alkylcarbonyl substituted by 1-4 groups $R^{13}$, heteroaryl$C_1$-$C_3$alkylcarbonyl and heteroaryl$C_1$-$C_3$alkylcarbonyl substituted by 1-3 groups $R^{13}$;

each $R^{13}$ is independently selected from the group consisting of halogen, $C_1$-$C_4$alkyl, $C_1$-$C_4$haloalkyl, $C_1$-$C_4$alkoxy, $C_1$-$C_4$haloalkoxy, cyano and $C_1$-$C_4$alkylsulfonyl;

$R^{14}$ is selected from the group consisting of $C_1$-$C_4$alkyl, $C_1$-$C_4$haloalkyl, and $C_1$-$C_4$alkyl($C_1$-$C_4$alkyl)amino;

$R^{15}$ is selected from the group consisting of hydrogen, $C_1$-$C_4$alkyl and $C_1$-$C_4$haloalkyl;

each $R^{16}$ is independently selected from the group consisting of hydrogen, $C_1$-$C_4$alkyl, $C_1$-$C_4$haloalkyl and $C_1$-$C_4$alkoxycarbonyl$C_1$-$C_4$alkyl.

According to a second aspect of the invention, there is provided an agrochemical composition comprising a herbicidally effective amount of a compound of formula (I) and an agrochemically-acceptable diluent or carrier. Such an agricultural composition may further comprise at least one additional active ingredient.

According to a third aspect of the invention, there is provided a method of controlling or preventing undesirable plant growth, wherein a herbicidally effective amount of a compound of formula (I), or a composition comprising this compound as active ingredient, is applied to the plants, to parts thereof or the locus thereof.

According to a fourth aspect of the invention, there is provided the use of a compound of formula (I) as a herbicide.

According to a fifth aspect of the invention, there is provided a process for the preparation of compounds of formula (I).

As used herein, the term "halogen" or "halo" refers to fluorine (fluoro), chlorine (chloro), bromine (bromo) or iodine (iodo), preferably fluorine, chlorine or bromine.

As used herein, cyano means a —CN group.

As used herein, hydroxy means an —OH group.

As used herein, nitro means an —$NO_2$ group.

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. $C_1$-$C_4$alkyl and $C_1$-$C_2$alkyl are to be construed accordingly. Examples of $C_1$-$C_6$alkyl include, but are not limited to, methyl (Me), ethyl (Et), n-propyl, 1-methylethyl (iso-propyl), n-butyl, and 1-dimethylethyl (t-butyl).

As used herein, the term "$C_1$-$C_6$alkoxy" refers to a radical of the formula —$OR_a$ where $R_a$ is a $C_1$-$C_6$alkyl radical as generally defined above. $C_1$-$C_4$alkoxy is to be construed accordingly. Examples of $C_{1-4}$alkoxy include, but are not limited to, methoxy, ethoxy, propoxy, iso-propoxy and t-butoxy.

As used herein, the term "$C_1$-$C_6$haloalkyl" refers to a $C_1$-$C_6$alkyl radical as generally defined above substituted by one or more of the same or different halogen atoms. $C_1$-$C_4$haloalkyl is to be construed accordingly. Examples of $C_1$-$C_6$haloalkyl include, but are not limited to chloromethyl, fluoromethyl, fluoroethyl, difluoromethyl, trifluoromethyl and 2,2,2-trifluoroethyl.

As used herein, the term "$C_2$-$C_6$alkenyl" refers to a straight or branched hydrocarbon chain radical group consisting solely of carbon and hydrogen atoms, containing at least one double bond that can be of either the (E)- or (Z)-configuration, having from two to six carbon atoms, which is attached to the rest of the molecule by a single bond. $C_2$-$C_4$alkenyl is to be construed accordingly. Examples of $C_2$-$C_6$alkenyl include, but are not limited to, prop-1-enyl, ally) (prop-2-enyl) and but-1-enyl.

As used herein, the term "$C_2$-$C_6$haloalkenyl" refers to a $C_2$-$C_6$alkenyl radical as generally defined above substituted by one or more of the same or different halogen atoms. Examples of $C_2$-$C_6$haloalkenyl include, but are not limited to chloroethylene, fluoroethylene, 1,1-difluoroethylene, 1,1-dichloroethylene and 1,1,2-trichloroethylene.

As used herein, the term "$C_2$-$C_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. $C_2$-$C_4$alkynyl is to be construed accordingly. Examples of $C_2$-$C_6$alkynyl include, but are not limited to, prop-1-ynyl, propargyl (prop-2-ynyl) and but-1-ynyl.

As used herein, the term "$C_1$-$C_6$haloalkoxy" refers to a $C_1$-$C_6$alkoxy group as defined above substituted by one or more of the same or different halogen atoms. $C_1$-$C_4$haloalkoxy is to be construed accordingly. Examples of $C_1$-$C_6$haloalkoxy include, but are not limited to, fluoromethoxy, difluoromethoxy, fluoroethoxy, trifluoromethoxy and trifluoroethoxy.

As used herein, the term "$C_1$-$C_3$haloalkoxy$C_1$-$C_3$alkyl" refers to a radical of the formula $R_b$—O—$R_a$— where $R_b$ is a $C_1$-$C_3$haloalkyl radical as generally defined above, and $R_a$ is a $C_1$-$C_3$alkylene radical as generally defined above.

As used herein, the term "$C_1$-$C_3$alkoxy$C_1$-$C_3$alkyl" refers to a radical of the formula $R_b$—O—$R_a$— where $R_b$ is a $C_1$-$C_3$alkyl radical as generally defined above, and $R_a$ is a $C_1$-$C_3$alkylene radical as generally defined above.

As used herein, the term "$C_1$-$C_3$alkoxy$C_1$-$C_3$alkoxy-" refers to a radical of the formula $R_b$—O—$R_a$—O— where $R_b$ is a $C_1$-$C_3$alkyl radical as generally defined above, and $R_a$ is a $C_1$-$C_3$alkylene radical as generally defined above.

As used herein, the term "$C_3$-$C_6$alkenyloxy" refers to a radical of the formula —$OR_a$ where $R_a$ is a $C_3$-$C_6$alkenyl radical as generally defined above.

As used herein, the term "$C_3$-$C_6$alkynyloxy" refers to a radical of the formula —$OR_a$ where $R_a$ is a $C_3$-$C_6$alkynyl radical as generally defined above.

As used herein, the term "hydroxy$C_1$-$C_6$alkyl" refers to a $C_1$-$C_6$alkyl radical as generally defined above substituted by one or more hydroxy groups.

As used herein, the term "$C_1$-$C_6$alkylcarbonyl" refers to a radical of the formula —$C(O)R_a$ where $R_a$ is a $C_1$-$C_6$alkyl radical as generally defined above.

As used herein, the term "$C_1$-$C_6$alkoxycarbonyl" refers to a radical of the formula —$C(O)OR_a$ where $R_a$ is a $C_1$-$C_6$alkyl radical as generally defined above.

As used herein, the term "aminocarbonyl" refers to a radical of the formula —$C(O)NH_2$.

As used herein, the term "aminothiocarbonyl" refers to a radical of the formula —$C(S)NH_2$.

As used herein, the term "$C_3$-$C_6$cycloalkyl" refers to a stable, monocyclic ring radical which is saturated or partially unsaturated and contains 3 to 6 carbon atoms. $C_3$-$C_4$cycloalkyl is to be construed accordingly. Examples of $C_3$-$C_6$cycloalkyl include, but are not limited to, cyclopropyl, cyclobutyl, cyclopentyl and cyclohexyl.

As used herein, the term "$C_3$-$C_6$halocycloalkyl" refers to a $C_3$-$C_6$cycloalkyl radical as generally defined above substituted by one or more of the same or different halogen atoms. $C_3$-$C_4$halocycloalkyl is to be construed accordingly.

As used herein, the term "$C_3$-$C_6$cycloalkoxy" refers to a radical of the formula —$OR_a$ where $R_a$ is a $C_3$-$C_6$cycloalkyl radical as generally defined above.

As used herein, the term "N—$C_3$-$C_6$cycloalkylamino" refers to a radical of the formula —$NHR_a$ where $R_a$ is a $C_3$-$C_6$cycloalkyl radical as generally defined above.

As used herein, except where explicitly stated otherwise, the term "heteroaryl" refers to a 5- or 6-membered monocyclic aromatic ring which comprises 1, 2, 3 or 4 heteroatoms individually selected from nitrogen, oxygen and sulfur. The heteroaryl radical may be bonded to the rest of the molecule via a carbon atom or heteroatom. Examples of heteroaryl include, fury, pyrrolyl, imidazolyl, thienyl, pyrazolyl, thiazolyl, isothiazolyl, oxazolyl, isoxazolyl, triazolyl, tetrazolyl, pyrazinyl, pyridazinyl, pyrimidyl or pyridyl.

As used herein, except where explicitly stated otherwise, the term "heterocyclyl" or "heterocyclic" refers to a stable 4- to 6-membered non-aromatic monocyclic ring radical which comprises 1, 2, or 3 heteroatoms individually selected from nitrogen, oxygen and sulfur. The heterocyclyl radical may be bonded to the rest of the molecule via a carbon atom or heteroatom. Examples of heterocyclyl include, but are not limited to, pyrrolinyl, pyrrolidyl, tetrahydrofuryl, tetrahydrothienyl, tetrahydrothiopyranyl, piperidyl, piperazinyl, tetrahydropyranyl, dihydroisoxazolyl, dioxolanyl, morpholinyl or o-lactamyl.

The presence of one or more possible asymmetric carbon atoms in a compound of formula (I) means that the compounds may occur in chiral isomeric forms, i.e., enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof fora compound of formula (I). Likewise, formula (I) is intended to include all possible tautomers (including lactam-lactim tautomerism and keto-enol tautomerism) where present. The present invention includes all possible tautomeric forms for a compound of formula (I). Similarly, where there are di-substituted alkenes, these may be present in E or Z form or as mixtures of both in any proportion. The present invention includes all these possible isomeric forms and mixtures thereof for a compound of formula (I).

The compounds of formula (I) will typically be provided in the form of an agronomically acceptable salt, a zwitterion or an agronomically acceptable salt of a zwitterion. This invention covers all such agronomically acceptable salts, zwitterions and mixtures thereof in all proportions.

Suitable agronomically acceptable salts of the present invention can be with cations that include but are not limited to, metals, conjugate acids of amines and organic cations. Examples of suitable metals include aluminium, calcium, cesium, copper, lithium, magnesium, manganese, potassium, sodium, iron and zinc. Examples of suitable amines include allylamine, ammonia, amylamine, arginine, benethamine, benzathine, butenyl-2-amine, butylamine, butylethanolamine, cyclohexylamine, decylamine, diamylamine, dibutylamine, diethanolamine, diethylamine, diethylenetriamine, diheptylamine, dihexylamine, diisoamylamine, diisopropylamine, dimethylamine, dioctylamine, dipropanolamine, dipropargylamine, dipropylamine, dodecylamine, ethanolamine, ethylamine, ethylbutylamine, ethylenediamine, ethylheptylamine, ethyloctylamine, ethylpropanolamine, heptadecylamine, heptylamine, hexadecylamine, hexenyl-2-amine, hexylamine, hexylheptylamine, hexyloctylamine, histidine, indoline, isoamylamine, isobutanolamine, isobutylamine, isopropanolamine, isopropylamine, lysine, meglumine, methoxyethylamine, methylamine, methylbutylamine, methylethylamine, methylhexylamine, methylisopropylamine, methylnonylamine, methyloctadecylamine, methylpentadecylamine, morpholine, N,N-diethylethanolamine, N-methylpiperazine, nonylamine, octadecylamine, octylamine, oleylamine, pentadecylamine, pentenyl-2-amine, phenoxyethylamine, picoline, piperazine, piperidine, propanolamine, propylamine, propylenediamine, pyridine, pyrrolidine, sec-butylamine, stearylamine, tallowamine, tetradecylamine, tributylamine, tridecylamine, trimethylamine, triheptylamine, trihexylamine, triisobutylamine, triisodecylamine, triisopropylamine, trimethylamine, tripentylamine, tripropylamine, tris(hydroxymethyl)aminomethane, and undecylamine. Examples of suitable organic cations include benzyltributylammonium, benzyltrimethylammonium, benzyltriphenylphosphonium, choline, tetrabutylammonium, tetrabutylphosphonium, tetraethylammonium, tetraethylphosphonium, tetramethylammonium, tetramethylphosphonium, tetrapropylammonium, tetrapropylphosphonium, tributylsulfonium, tributylsulfoxonium, triethylsulfonium, triethylsulfoxonium, trimethylsulfonium, trimethylsulfoxonium, tripropylsulfonium and tripropylsulfoxonium.

The following list provides definitions, including preferred definitions, for substituents X, Y, Z, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ with reference to the compounds of formula (I) according to the invention. For any one of these substituents, any of the definitions given below may be combined with any definition of any other substituent given below or elsewhere in this document.

Preferably X is sulfur.
Preferably Y is C—H.
Preferably $R^1$ is selected from the group consisting of hydrogen and $C_1$-$C_4$alkyl, more preferably $C_1$-$C_2$alkyl, most preferably methyl.
Preferably $R^2$ is selected from the group consisting of hydrogen, $C_1$-$C_4$alkyl and $C_3$-$C_4$alkynyl, more preferably $C_1$-$C_2$alkyl, most preferably methyl.
Preferably $R^3$ is selected from the group consisting of hydrogen, chlorine and fluorine, more preferably chlorine and fluorine.
Preferably $R^4$ is selected from the group consisting of hydrogen, chlorine, cyano and aminothiocarbonyl, more preferably chlorine, cyano and aminothiocarbonyl, most preferably chlorine.

Preferably each $R^5$ and $R^6$ is independently selected from the group consisting of hydrogen, $C_1$-$C_4$alkyl, $CO_2R^9$ and $CH_2OR^{12}$, more preferably hydrogen and $C_1$-$C_2$alkyl, most preferably hydrogen.
Preferably each $R^7$ and $R^8$ is independently selected from the group consisting of hydrogen, $C_1$-$C_4$alkyl, $C_1$-$C_6$haloalkyl, $CO_2R^9$, $CONR^{10}R^{11}$ and $CH_2OR^{12}$. More preferably $R^7$ is selected from the group consisting of $CO_2R^9$, $CONR^{10}R^{11}$ and $CH_2OR^{12}$, most preferably $CO_2R^9$. More preferably $R^8$ is selected from the group consisting of hydrogen and $C_1$-$C_4$alkyl, most preferably methyl.
Preferably $R^9$ is selected from the group consisting of hydrogen, $C_1$-$C_4$alkyl, $C_1$-$C_4$haloalkyl, $C_1$-$C_2$alkoxy$C_1$-$C_2$alkyl, phenyl$C_1$-$C_2$alkyl and phenyl$C_1$-$C_2$alkyl substituted by 1-2 groups $R^{13}$, more preferably hydrogen, $C_1$-$C_4$alkyl, $C_1$-$C_2$alkoxy$C_1$-$C_2$alkyl and phenyl$C_1$-$C_2$alkyl, most preferably hydrogen, $C_1$-$C_4$alkyl and phenyl$C_1$-$C_2$alkyl.
Preferably $R^{10}$ is selected from the group consisting of hydrogen and $SO_2R^{14}$, more preferably $SO_2R^{14}$. Preferably $R^{11}$ is hydrogen.
Preferably $R^{12}$ is selected from the group consisting of hydrogen, $C_1$-$C_2$alkyl, $C_1$-$C_2$alkylsulfonyl, $C_1$-$C_2$haloalkylsulfonyl, $C_1$-$C_4$alkylcarbonyl, phenylcarbonyl, phenylcarbonyl substituted by 1-2 groups $R^{13}$, phenyl$C_1$-$C_2$alkylcarbonyl and phenyl$C_1$-$C_2$alkylcarbonyl substituted by 1-2 groups $R^{13}$ more preferably $C_1$-$C_2$alkylsulfonyl, $C_1$-$C_2$haloalkylsulfonyl and $C_1$-$C_4$alkylcarbonyl.
Preferably $R^{13}$ is selected from the group consisting of halogen, $C_1$-$C_4$alkyl, $C_1$-$C_4$haloalkyl, $C_1$-$C_4$alkoxy, $C_1$-$C_4$haloalkoxy, cyano and $C_1$-$C_4$alkylsulfonyl.
Preferably $R^{14}$ is selected from the group consisting of $C_1$-$C_4$alkyl and $C_1$-$C_4$alkyl($C_1$-$C_4$alkyl)amino, more preferably methyl and isopropyl(methyl)amino.

A preferred subset of compounds is one in which;
X is sulfur;
Y is C—H;
$R^1$ is $C_1$-$C_2$alkyl;
$R^2$ is $C_1$-$C_2$alkyl;
$R^3$ is selected from the group consisting of hydrogen, chlorine and fluorine;
$R^4$ is selected from the group consisting of chlorine, cyano and aminothiocarbonyl;
each $R^5$ and $R^6$ is independently selected from the group consisting of hydrogen and $C_1$-$C_2$alkyl;
$R^7$ is selected from the group consisting of $CO_2R^9$, $CONR^{10}R^{11}$ and $CH_2OR^{12}$;
$R^8$ is selected from the group consisting of hydrogen and $C_1$-$C_4$alkyl;
$R^9$ is selected from the group consisting of hydrogen, $C_1$-$C_4$alkyl, $C_1$-$C_2$alkoxy$C_1$-$C_2$alkyl and phenyl$C_1$-$C_2$alkyl;
$R^{10}$ is $SO_2R^{14}$;
$R^{11}$ is hydrogen.
$R^{12}$ is selected from the group consisting of $C_1$-$C_2$alkylsulfonyl, $C_1$-$C_2$haloalkylsulfonyl and $C_1$-$C_4$alkylcarbonyl;
$R^{14}$ is selected from the group consisting of methyl and isopropyl(methyl)amino.

A more preferred subset of compounds is one in which;
X is sulfur;
Y is C—H;
$R^1$ is methyl;
$R^2$ is methyl;
$R^3$ is selected from the group consisting of chlorine and fluorine;

$R^4$ is chlorine;

each $R^5$ and $R^6$ is hydrogen;

$R^7$ is $CO_2R^9$;

$R^8$ is methyl;

$R^9$ is selected from the group consisting of hydrogen, $C_1$-$C_4$alkyl and phenyl$C_1$-$C_2$alkyl.

Table of Examples
This table discloses specific compounds of formula (I), wherein $R^1$ and $R^2$ are methyl.

| Compound Number | X | $R^3$ | $R^4$ | $R^5$ | $R^6$ | $R^7$ | $R^8$ |
|---|---|---|---|---|---|---|---|
| 1 | O | H | Cl | H | H | $CO_2H$ | Me |
| 2 | O | H | Cl | H | H | $CO_2Me$ | Me |
| 3 | O | H | Cl | H | H | $CO_2Et$ | Me |
| 4 | O | H | Cl | H | H | $CO_2CH_2Ph$ | Me |
| 5 | O | H | Cl | H | H | $CH_2OH$ | Me |
| 6 | O | H | Cl | H | H | $CH_2OMe$ | Me |
| 7 | O | H | Cl | H | H | $CH_2OCOMe$ | Me |
| 8 | O | H | Cl | H | H | $CH_2OCOPh$ | Me |
| 9 | O | H | Cl | H | H | $CH_2OSO_2Me$ | Me |
| 10 | O | H | Cl | H | H | $CH_2OSO_2CF_3$ | Me |
| 11 | O | H | Cl | H | H | $CH_2OSO_2(4MePh)$ | Me |
| 12 | O | F | Cl | H | H | $CO_2H$ | Me |
| 13 | O | F | Cl | H | H | $CO_2Me$ | Me |
| 14 | O | F | Cl | H | H | $CO_2Et$ | Me |
| 15 | O | F | Cl | H | H | $CO_2CH_2Ph$ | Me |
| 16 | O | F | Cl | H | H | $CH_2OH$ | Me |
| 17 | O | F | Cl | H | H | $CH_2OMe$ | Me |
| 18 | O | F | Cl | H | H | $CH_2OCOMe$ | Me |
| 19 | O | F | Cl | H | H | $CH_2OCOPh$ | Me |
| 20 | O | F | Cl | H | H | $CH_2OSO_2Me$ | Me |
| 21 | O | F | Cl | H | H | $CH_2OSO_2CF_3$ | Me |
| 22 | O | F | Cl | H | H | $CH_2OSO_2(4MePh)$ | Me |
| 23 | O | Cl | Cl | H | H | $CO_2H$ | Me |
| 24 | O | Cl | Cl | H | H | $CO_2Me$ | Me |
| 25 | O | Cl | Cl | H | H | $CO_2Et$ | Me |
| 26 | O | Cl | Cl | H | H | $CO_2CH_2Ph$ | Me |
| 27 | O | Cl | Cl | H | H | $CH_2OH$ | Me |
| 28 | O | Cl | Cl | H | H | $CH_2OMe$ | Me |
| 29 | O | Cl | Cl | H | H | $CH_2OCOMe$ | Me |
| 30 | O | Cl | Cl | H | H | $CH_2OCOPh$ | Me |
| 31 | O | Cl | Cl | H | H | $CH_2OSO_2Me$ | Me |
| 32 | O | Cl | Cl | H | H | $CH_2OSO_2CF_3$ | Me |
| 33 | O | Cl | Cl | H | H | $CH_2OSO_2(4MePh)$ | Me |
| 34 | S | H | Cl | H | H | $CO_2H$ | Me |
| 35 | S | H | Cl | H | H | $CO_2Me$ | Me |
| 36 | S | H | Cl | H | H | $CO_2Et$ | Me |
| 37 | S | H | Cl | H | H | $CO_2CH_2Ph$ | Me |
| 38 | S | H | Cl | H | H | $CH_2OH$ | Me |
| 39 | S | H | Cl | H | H | $CH_2OMe$ | Me |
| 40 | S | H | Cl | H | H | $CH_2OCOMe$ | Me |
| 41 | S | H | Cl | H | H | $CH_2OCOPh$ | Me |
| 42 | S | H | Cl | H | H | $CH_2OSO_2Me$ | Me |
| 43 | S | H | Cl | H | H | $CH_2OSO_2CF_3$ | Me |
| 44 | S | H | Cl | H | H | $CH_2OSO_2(4MePh)$ | Me |
| 45 | S | F | Cl | H | H | $CO_2H$ | Me |
| 46 | S | F | Cl | H | H | $CO_2Me$ | Me |
| 47 | S | F | Cl | H | H | $CO_2Et$ | Me |
| 48 | S | F | Cl | H | H | $CO_2CH_2Ph$ | Me |
| 49 | S | F | Cl | H | H | $CH_2OH$ | Me |
| 50 | S | F | Cl | H | H | $CH_2OMe$ | Me |
| 51 | S | F | Cl | H | H | $CH_2OCOMe$ | Me |
| 52 | S | F | Cl | H | H | $CH_2OCOPh$ | Me |
| 53 | S | F | Cl | H | H | $CH_2OSO_2Me$ | Me |
| 54 | S | F | Cl | H | H | $CH_2OSO_2CF_3$ | Me |
| 55 | S | F | Cl | H | H | $CH_2OSO_2(4MePh)$ | Me |
| 56 | S | Cl | Cl | H | H | $CO_2H$ | Me |
| 57 | S | Cl | Cl | H | H | $CO_2Me$ | Me |
| 58 | S | Cl | Cl | H | H | $CO_2Et$ | Me |
| 59 | S | Cl | Cl | H | H | $CO_2CH_2Ph$ | Me |
| 60 | S | Cl | Cl | H | H | $CH_2OH$ | Me |
| 61 | S | Cl | Cl | H | H | $CH_2OMe$ | Me |
| 62 | S | Cl | Cl | H | H | $CH_2OCOMe$ | Me |
| 63 | S | Cl | Cl | H | H | $CH_2OCOPh$ | Me |
| 64 | S | Cl | Cl | H | H | $CH_2OSO_2Me$ | Me |
| 65 | S | Cl | Cl | H | H | $CH_2OSO_2CF_3$ | Me |
| 66 | S | Cl | Cl | H | H | $CH_2OSO_2(4MePh)$ | Me |
| 67 | S | H | CN | H | H | $CO_2H$ | Me |
| 68 | S | H | CN | H | H | $CO_2Me$ | Me |
| 69 | S | H | CN | H | H | $CO_2Et$ | Me |
| 70 | S | H | CN | H | H | $CO_2CH_2Ph$ | Me |
| 71 | S | H | CN | H | H | $CH_2OH$ | Me |
| 72 | S | H | CN | H | H | $CH_2OMe$ | Me |
| 73 | S | H | CN | H | H | $CH_2OCOMe$ | Me |
| 74 | S | H | CN | H | H | $CH_2OCOPh$ | Me |
| 75 | S | H | CN | H | H | $CH_2OSO_2Me$ | Me |
| 76 | S | H | CN | H | H | $CH_2OSO_2CF_3$ | Me |
| 77 | S | H | CN | H | H | $CH_2OSO_2(4MePh)$ | Me |
| 78 | S | F | CN | H | H | $CO_2H$ | Me |
| 79 | S | F | CN | H | H | $CO_2Me$ | Me |
| 80 | S | F | CN | H | H | $CO_2Et$ | Me |
| 81 | S | F | CN | H | H | $CO_2CH_2Ph$ | Me |
| 82 | S | F | CN | H | H | $CH_2OH$ | Me |
| 83 | S | F | CN | H | H | $CH_2OMe$ | Me |
| 84 | S | F | CN | H | H | $CH_2OCOMe$ | Me |
| 85 | S | F | CN | H | H | $CH_2OCOPh$ | Me |
| 86 | S | F | CN | H | H | $CH_2OSO_2Me$ | Me |
| 87 | S | F | CN | H | H | $CH_2OSO_2CF_3$ | Me |
| 88 | S | F | CN | H | H | $CH_2OSO_2(4MePh)$ | Me |
| 89 | S | Cl | CN | H | H | $CO_2H$ | Me |
| 90 | S | Cl | CN | H | H | $CO_2Me$ | Me |
| 91 | S | Cl | CN | H | H | $CO_2Et$ | Me |
| 92 | S | Cl | CN | H | H | $CO_2CH_2Ph$ | Me |
| 93 | S | Cl | CN | H | H | $CH_2OH$ | Me |
| 94 | S | Cl | CN | H | H | $CH_2OMe$ | Me |
| 95 | S | Cl | CN | H | H | $CH_2OCOMe$ | Me |
| 96 | S | Cl | CN | H | H | $CH_2OCOPh$ | Me |
| 97 | S | Cl | CN | H | H | $CH_2OSO_2Me$ | Me |
| 98 | S | Cl | CN | H | H | $CH_2OSO_2CF_3$ | Me |
| 99 | S | Cl | CN | H | H | $CH_2OSO_2(4MePh)$ | Me |
| 100 | S | H | $CSNH_2$ | H | H | $CO_2H$ | Me |
| 101 | S | H | $CSNH_2$ | H | H | $CO_2Me$ | Me |
| 102 | S | H | $CSNH_2$ | H | H | $CO_2Et$ | Me |
| 103 | S | H | $CSNH_2$ | H | H | $CO_2CH_2Ph$ | Me |
| 104 | S | H | $CSNH_2$ | H | H | $CH_2OH$ | Me |
| 105 | S | H | $CSNH_2$ | H | H | $CH_2OMe$ | Me |
| 106 | S | H | $CSNH_2$ | H | H | $CH_2OCOMe$ | Me |
| 107 | S | H | $CSNH_2$ | H | H | $CH_2OCOPh$ | Me |
| 108 | S | H | $CSNH_2$ | H | H | $CH_2OSO_2Me$ | Me |
| 109 | S | H | $CSNH_2$ | H | H | $CH_2OSO_2CF_3$ | Me |
| 110 | S | H | $CSNH_2$ | H | H | $CH_2OSO_2(4MePh)$ | Me |
| 111 | S | F | $CSNH_2$ | H | H | $CO_2H$ | Me |
| 112 | S | F | $CSNH_2$ | H | H | $CO_2Me$ | Me |
| 113 | S | F | $CSNH_2$ | H | H | $CO_2Et$ | Me |
| 114 | S | F | $CSNH_2$ | H | H | $CO_2CH_2Ph$ | Me |
| 115 | S | F | $CSNH_2$ | H | H | $CH_2OH$ | Me |
| 116 | S | F | $CSNH_2$ | H | H | $CH_2OMe$ | Me |
| 117 | S | F | $CSNH_2$ | H | H | $CH_2OCOMe$ | Me |
| 118 | S | F | $CSNH_2$ | H | H | $CH_2OCOPh$ | Me |
| 119 | S | F | $CSNH_2$ | H | H | $CH_2OSO_2Me$ | Me |
| 120 | S | F | $CSNH_2$ | H | H | $CH_2OSO_2CF_3$ | Me |
| 121 | S | F | $CSNH_2$ | H | H | $CH_2OSO_2(4MePh)$ | Me |
| 122 | S | Cl | $CSNH_2$ | H | H | $CO_2H$ | Me |
| 123 | S | Cl | $CSNH_2$ | H | H | $CO_2Me$ | Me |
| 124 | S | Cl | $CSNH_2$ | H | H | $CO_2Et$ | Me |
| 125 | S | Cl | $CSNH_2$ | H | H | $CO_2CH_2Ph$ | Me |
| 126 | S | Cl | $CSNH_2$ | H | H | $CH_2OH$ | Me |
| 127 | S | Cl | $CSNH_2$ | H | H | $CH_2OMe$ | Me |
| 128 | S | Cl | $CSNH_2$ | H | H | $CH_2OCOMe$ | Me |
| 129 | S | Cl | $CSNH_2$ | H | H | $CH_2OCOPh$ | Me |
| 130 | S | Cl | $CSNH_2$ | H | H | $CH_2OSO_2Me$ | Me |
| 131 | S | Cl | $CSNH_2$ | H | H | $CH_2OSO_2CF_3$ | Me |
| 132 | S | Cl | $CSNH_2$ | H | H | $CH_2OSO_2(4MePh)$ | Me |
| 133 | S | H | Cl | Me | H | $CO_2H$ | Me |

Table of Examples
This table discloses specific compounds of formula (I), wherein $R^1$ and $R^2$ are methyl.

| Compound Number | X | $R^3$ | $R^4$ | $R^5$ | $R^6$ | $R^7$ | $R^8$ |
|---|---|---|---|---|---|---|---|
| 134 | S | H | Cl | Me | H | $CO_2Me$ | Me |
| 135 | S | H | Cl | Me | H | $CO_2Et$ | Me |
| 136 | S | H | Cl | Me | H | $CO_2CH_2Ph$ | Me |
| 137 | S | H | Cl | Me | H | $CH_2OH$ | Me |
| 138 | S | H | Cl | Me | H | $CH_2OMe$ | Me |
| 139 | S | H | Cl | Me | H | $CH_2OCOMe$ | Me |
| 140 | S | H | Cl | Me | H | $CH_2OCOPh$ | Me |
| 141 | S | H | Cl | Me | H | $CH_2OSO_2Me$ | Me |
| 142 | S | H | Cl | Me | H | $CH_2OSO_2CF_3$ | Me |
| 143 | S | H | Cl | Me | H | $CH_2OSO_2(4MePh)$ | Me |
| 144 | S | F | Cl | Me | H | $CO_2H$ | Me |
| 145 | S | F | Cl | Me | H | $CO_2Me$ | Me |
| 146 | S | F | Cl | Me | H | $CO_2Et$ | Me |
| 147 | S | F | Cl | Me | H | $CO_2CH_2Ph$ | Me |
| 148 | S | F | Cl | Me | H | $CH_2OH$ | Me |
| 149 | S | F | Cl | Me | H | $CH_2OMe$ | Me |
| 150 | S | F | Cl | Me | H | $CH_2OCOMe$ | Me |
| 151 | S | F | Cl | Me | H | $CH_2OCOPh$ | Me |
| 152 | S | F | Cl | Me | H | $CH_2OSO_2Me$ | Me |
| 153 | S | F | Cl | Me | H | $CH_2OSO_2CF_3$ | Me |
| 154 | S | F | Cl | Me | H | $CH_2OSO_2(4MePh)$ | Me |
| 155 | S | Cl | Cl | Me | H | $CO_2H$ | Me |
| 156 | S | Cl | Cl | Me | H | $CO_2Me$ | Me |
| 157 | S | Cl | Cl | Me | H | $CO_2Et$ | Me |
| 158 | S | Cl | Cl | Me | H | $CO_2CH_2Ph$ | Me |
| 159 | S | Cl | Cl | Me | H | $CH_2OH$ | Me |
| 160 | S | Cl | Cl | Me | H | $CH_2OMe$ | Me |
| 161 | S | Cl | Cl | Me | H | $CH_2OCOMe$ | Me |
| 162 | S | Cl | Cl | Me | H | $CH_2OCOPh$ | Me |
| 163 | S | Cl | Cl | Me | H | $CH_2OSO_2Me$ | Me |
| 164 | S | Cl | Cl | Me | H | $CH_2OSO_2CF_3$ | Me |
| 165 | S | Cl | Cl | Me | H | $CH_2OSO_2(4MePh)$ | Me |
| 166 | S | H | Cl | Me | Me | $CO_2H$ | Me |
| 167 | S | H | Cl | Me | Me | $CO_2Me$ | Me |
| 168 | S | H | Cl | Me | Me | $CO_2Et$ | Me |
| 169 | S | H | Cl | Me | Me | $CO_2CH_2Ph$ | Me |
| 170 | S | H | Cl | Me | Me | $CH_2OH$ | Me |
| 171 | S | H | Cl | Me | Me | $CH_2OMe$ | Me |
| 172 | S | H | Cl | Me | Me | $CH_2OCOMe$ | Me |
| 173 | S | H | Cl | Me | Me | $CH_2OCOPh$ | Me |
| 174 | S | H | Cl | Me | Me | $CH_2OSO_2Me$ | Me |
| 175 | S | H | Cl | Me | Me | $CH_2OSO_2CF_3$ | Me |
| 176 | S | H | Cl | Me | Me | $CH_2OSO_2(4MePh)$ | Me |
| 177 | S | F | Cl | Me | Me | $CO_2H$ | Me |
| 178 | S | F | Cl | Me | Me | $CO_2Me$ | Me |
| 179 | S | F | Cl | Me | Me | $CO_2Et$ | Me |
| 180 | S | F | Cl | Me | Me | $CO_2CH_2Ph$ | Me |
| 181 | S | F | Cl | Me | Me | $CH_2OH$ | Me |
| 182 | S | F | Cl | Me | Me | $CH_2OMe$ | Me |
| 183 | S | F | Cl | Me | Me | $CH_2OCOMe$ | Me |
| 184 | S | F | Cl | Me | Me | $CH_2OCOPh$ | Me |
| 185 | S | F | Cl | Me | Me | $CH_2OSO_2Me$ | Me |
| 186 | S | F | Cl | Me | Me | $CH_2OSO_2CF_3$ | Me |
| 187 | S | F | Cl | Me | Me | $CH_2OSO_2(4MePh)$ | Me |
| 188 | S | Cl | Cl | Me | Me | $CO_2H$ | Me |
| 189 | S | Cl | Cl | Me | Me | $CO_2Me$ | Me |
| 190 | S | Cl | Cl | Me | Me | $CO_2Et$ | Me |
| 191 | S | Cl | Cl | Me | Me | $CO_2CH_2Ph$ | Me |
| 192 | S | Cl | Cl | Me | Me | $CH_2OH$ | Me |
| 193 | S | Cl | Cl | Me | Me | $CH_2OMe$ | Me |
| 194 | S | Cl | Cl | Me | Me | $CH_2OCOMe$ | Me |
| 195 | S | Cl | Cl | Me | Me | $CH_2OCOPh$ | Me |
| 196 | S | Cl | Cl | Me | Me | $CH_2OSO_2Me$ | Me |
| 197 | S | Cl | Cl | Me | Me | $CH_2OSO_2CF_3$ | Me |
| 198 | S | Cl | Cl | Me | Me | $CH_2OSO_2(4MePh)$ | Me |
| 199 | S | H | Cl | H | H | $CO_2H$ | H |
| 200 | S | H | Cl | H | H | $CO_2Me$ | H |
| 201 | S | H | Cl | H | H | $CO_2Et$ | H |
| 202 | S | H | Cl | H | H | $CO_2CH_2Ph$ | H |
| 203 | S | H | Cl | H | H | $CH_2OH$ | H |
| 204 | S | H | Cl | H | H | $CH_2OMe$ | H |
| 205 | S | H | Cl | H | H | $CH_2OCOMe$ | H |
| 206 | S | H | Cl | H | H | $CH_2OCOPh$ | H |
| 207 | S | H | Cl | H | H | $CH_2OSO_2Me$ | H |
| 208 | S | H | Cl | H | H | $CH_2OSO_2CF_3$ | H |
| 209 | S | H | Cl | H | H | $CH_2OSO_2(4MePh)$ | H |
| 210 | S | F | Cl | H | H | $CO_2H$ | H |
| 211 | S | F | Cl | H | H | $CO_2Me$ | H |
| 212 | S | F | Cl | H | H | $CO_2Et$ | H |
| 213 | S | F | Cl | H | H | $CO_2CH_2Ph$ | H |
| 214 | S | F | Cl | H | H | $CH_2OH$ | H |
| 215 | S | F | Cl | H | H | $CH_2OMe$ | H |
| 216 | S | F | Cl | H | H | $CH_2OCOMe$ | H |
| 217 | S | F | Cl | H | H | $CH_2OCOPh$ | H |
| 218 | S | F | Cl | H | H | $CH_2OSO_2Me$ | H |
| 219 | S | F | Cl | H | H | $CH_2OSO_2CF_3$ | H |
| 220 | S | F | Cl | H | H | $CH_2OSO_2(4MePh)$ | H |
| 221 | S | Cl | Cl | H | H | $CO_2H$ | H |
| 222 | S | Cl | Cl | H | H | $CO_2Me$ | H |
| 223 | S | Cl | Cl | H | H | $CO_2Et$ | H |
| 224 | S | Cl | Cl | H | H | $CO_2CH_2Ph$ | H |
| 225 | S | Cl | Cl | H | H | $CH_2OH$ | H |
| 226 | S | Cl | Cl | H | H | $CH_2OMe$ | H |
| 227 | S | Cl | Cl | H | H | $CH_2OCOMe$ | H |
| 228 | S | Cl | Cl | H | H | $CH_2OCOPh$ | H |
| 229 | S | Cl | Cl | H | H | $CH_2OSO_2Me$ | H |
| 230 | S | Cl | Cl | H | H | $CH_2OSO_2CF_3$ | H |
| 231 | S | Cl | Cl | H | H | $CH_2OSO_2(4MePh)$ | H |
| 232 | S | H | Cl | $CO_2H$ | Me | H | H |
| 233 | S | F | Cl | $CO_2H$ | Me | H | H |
| 234 | S | Cl | Cl | $CO_2H$ | Me | H | H |
| 235 | S | H | Cl | $CO_2Et$ | Me | H | H |
| 236 | S | F | Cl | $CO_2Et$ | Me | H | H |
| 237 | S | Cl | Cl | $CO_2Et$ | Me | H | H |
| 238 | S | H | Cl | $CH_2OH$ | Me | H | H |
| 239 | S | F | Cl | $CH_2OH$ | Me | H | H |
| 240 | S | Cl | Cl | $CH_2OH$ | Me | H | H |
| 241 | S | H | Cl | $CO_2H$ | Me | H | Me |
| 242 | S | F | Cl | $CO_2H$ | Me | H | Me |
| 243 | S | Cl | Cl | $CO_2H$ | Me | H | Me |
| 244 | S | H | Cl | $CO_2Et$ | Me | H | Me |
| 245 | S | F | Cl | $CO_2Et$ | Me | H | Me |
| 246 | S | Cl | Cl | $CO_2Et$ | Me | H | Me |
| 247 | S | H | Cl | $CH_2OH$ | Me | H | Me |
| 248 | S | F | Cl | $CH_2OH$ | Me | H | Me |
| 249 | S | Cl | Cl | $CH_2OH$ | Me | H | Me |
| 250 | S | H | Cl | H | H | $CO_2H$ | $CF_3$ |
| 251 | S | H | Cl | H | H | $CO_2Me$ | $CF_3$ |
| 252 | S | H | Cl | H | H | $CO_2Et$ | $CF_3$ |
| 253 | S | H | Cl | H | H | $CO_2CH_2Ph$ | $CF_3$ |
| 254 | S | H | Cl | H | H | $CH_2OH$ | $CF_3$ |
| 255 | S | H | Cl | H | H | $CH_2OMe$ | $CF_3$ |
| 256 | S | H | Cl | H | H | $CH_2OCOMe$ | $CF_3$ |
| 257 | S | H | Cl | H | H | $CH_2OCOPh$ | $CF_3$ |
| 258 | S | H | Cl | H | H | $CH_2OSO_2Me$ | $CF_3$ |
| 259 | S | H | Cl | H | H | $CH_2OSO_2CF_3$ | $CF_3$ |
| 260 | S | H | Cl | H | H | $CH_2OSO_2(4MePh)$ | $CF_3$ |
| 261 | S | F | Cl | H | H | $CO_2H$ | $CF_3$ |
| 262 | S | F | Cl | H | H | $CO_2Me$ | $CF_3$ |
| 263 | S | F | Cl | H | H | $CO_2Et$ | $CF_3$ |
| 264 | S | F | Cl | H | H | $CO_2CH_2Ph$ | $CF_3$ |
| 265 | S | F | Cl | H | H | $CH_2OH$ | $CF_3$ |
| 266 | S | F | Cl | H | H | $CH_2OMe$ | $CF_3$ |
| 267 | S | F | Cl | H | H | $CH_2OCOMe$ | $CF_3$ |
| 268 | S | F | Cl | H | H | $CH_2OCOPh$ | $CF_3$ |
| 269 | S | F | Cl | H | H | $CH_2OSO_2Me$ | $CF_3$ |
| 270 | S | F | Cl | H | H | $CH_2OSO_2CF_3$ | $CF_3$ |
| 271 | S | F | Cl | H | H | $CH_2OSO_2(4MePh)$ | $CF_3$ |
| 272 | S | Cl | Cl | H | H | $CO_2H$ | $CF_3$ |
| 273 | S | Cl | Cl | H | H | $CO_2Me$ | $CF_3$ |

Table of Examples
This table discloses specific compounds of formula (I), wherein $R^1$ and $R^2$ are methyl.

| Compound Number | X | $R^3$ | $R^4$ | $R^5$ | $R^6$ | $R^7$ | $R^8$ |
|---|---|---|---|---|---|---|---|
| 274 | S | Cl | Cl | H | H | $CO_2Et$ | $CF_3$ |
| 275 | S | Cl | Cl | H | H | $CO_2CH_2Ph$ | $CF_3$ |
| 276 | S | Cl | Cl | H | H | $CH_2OH$ | $CF_3$ |
| 277 | S | Cl | Cl | H | H | $CH_2OMe$ | $CF_3$ |
| 278 | S | Cl | Cl | H | H | $CH_2OCOMe$ | $CF_3$ |
| 279 | S | Cl | Cl | H | H | $CH_2OCOPh$ | $CF_3$ |
| 280 | S | Cl | Cl | H | H | $CH_2OSO_2Me$ | $CF_3$ |
| 281 | S | Cl | Cl | H | H | $CH_2OSO_2CF_3$ | $CF_3$ |
| 282 | S | Cl | Cl | H | H | $CH_2OSO_2(4MePh)$ | $CF_3$ |
| 283 | S | H | Cl | H | H | $CONHSO_2Me$ | Me |
| 284 | S | F | Cl | H | H | $CONHSO_2Me$ | Me |
| 285 | S | Cl | Cl | H | H | $CONHSO_2Me$ | Me |
| 286 | S | H | Cl | H | H | $CONHSO_2N(Me)(CHMe_2)$ | Me |
| 287 | S | F | Cl | H | H | $CONHSO_2N(Me)(CHMe_2)$ | Me |
| 288 | S | Cl | Cl | H | H | $CONHSO_2N(Me)(CHMe_2)$ | Me |
| 289 | S | H | Cl | H | H | COMe | Me |
| 290 | S | F | Cl | H | H | COMe | Me |
| 291 | S | Cl | Cl | H | H | COMe | Me |
| 292 | S | H | Cl | H | H | C(NOMe)Me | Me |
| 293 | S | F | Cl | H | H | C(NOMe)Me | Me |
| 294 | S | Cl | Cl | H | H | C(NOMe)Me | Me |
| 295 | S | H | Cl | H | H | C(NOH)Me | Me |
| 296 | S | F | Cl | H | H | C(NOH)Me | Me |
| 297 | S | Cl | Cl | H | H | C(NOH)Me | Me |
| 298 | S | H | Cl | H | H | $C(NOCH_2CO_2Me)Me$ | Me |
| 299 | S | F | Cl | H | H | $C(NOCH_2CO_2Me)Me$ | Me |
| 300 | S | Cl | Cl | H | H | $C(NOCH_2CO_2Me)Me$ | Me |
| 301 | S | H | Cl | H | H | $C(NNH_2)Me$ | Me |
| 302 | S | F | Cl | H | H | $C(NNH_2)Me$ | Me |
| 303 | S | Cl | Cl | H | H | $C(NNH_2)Me$ | Me |
| 304 | S | H | Cl | H | H | $CONHSO_2NMe_2$ | Me |
| 305 | S | F | Cl | H | H | $CONHSO_2NMe_2$ | Me |
| 306 | S | Cl | Cl | H | H | $CONHSO_2NMe_2$ | Me |
| 307 | S | H | Cl | H | H | $CONH_2$ | Me |
| 308 | S | F | Cl | H | H | $CONH_2$ | Me |
| 309 | S | Cl | Cl | H | H | $CONH_2$ | Me |
| 310 | S | H | Cl | H | H | $CO_2Me$ | OMe |
| 311 | S | F | Cl | H | H | $CO_2Me$ | OMe |
| 312 | S | Cl | Cl | H | H | $CO_2Me$ | OMe |

Compounds of the invention may be prepared by techniques known to the person skilled in the art of organic chemistry. General methods for the production of compounds of formula (I) are described below. Unless otherwise stated in the text, the substituents X, Y, Z, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are as defined hereinbefore. The starting materials used for the preparation of the compounds of the invention may be purchased from usual commercial suppliers or may be prepared by known methods. The starting materials as well as the intermediates may be purified before use in the next step by state of the art methodologies such as chromatography, crystallization, distillation and filtration.

Compounds of formula (I) may be prepared from compounds of formula (A) and compounds of formula (B) as shown in reaction scheme 1.

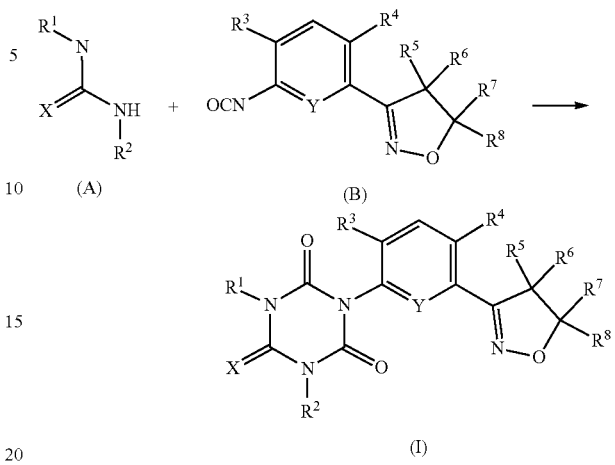

For example, a mixture of a compound of formula (A) and a compound of formula (B) may be treated with a base, such as triethylamine, and a carbonyl transfer reagent, such as phosgene or carbonyl diimidazole, in a suitable solvent such as toluene.

Ureas or thioureas of formula (A) are available or may be prepared by methods well known in the literature.

Compounds of formula (B) may be prepared from anilines of formula (C) as shown in reaction scheme 2.

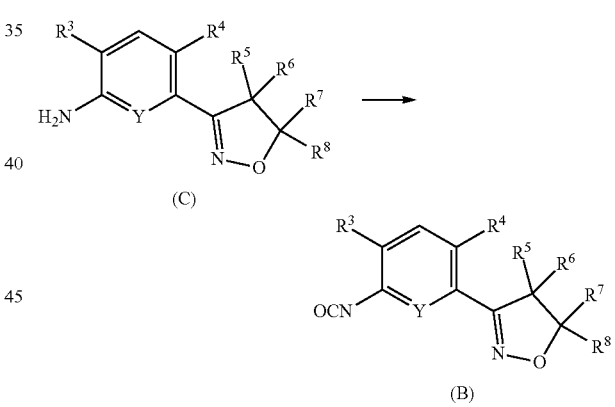

For example, a compound of formula (C) may be treated with a carbonyl transfer reagent, such as diphosgene or triphosgene, in a suitable solvent, such as toluene.

Anilines of formula (C) may be prepared from nitro compounds of formula (D) as shown in reaction scheme 3.

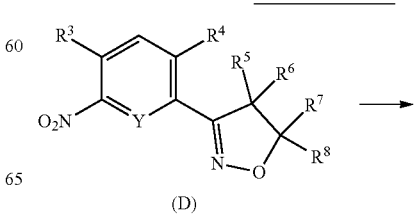

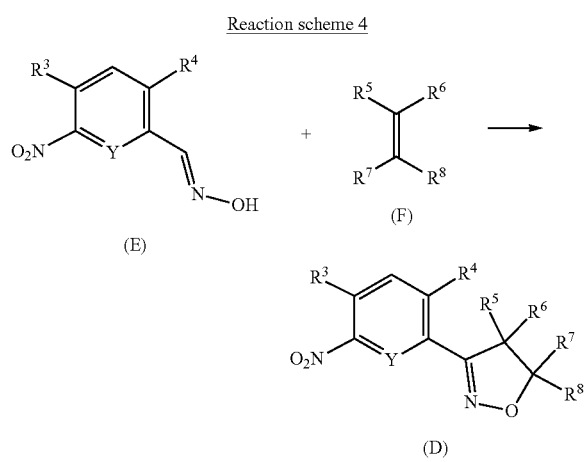

(C)

For example, a compound of formula (D) can be treated with a reducing agent, such as iron and ammonium chloride, in a suitable solvent, such as a mixture of water and ethanol.

Nitro compounds of formula (D) may be prepared from oximes of formula (E) and alkenes of formula (F) as shown in reaction scheme 4.

Reaction scheme 4

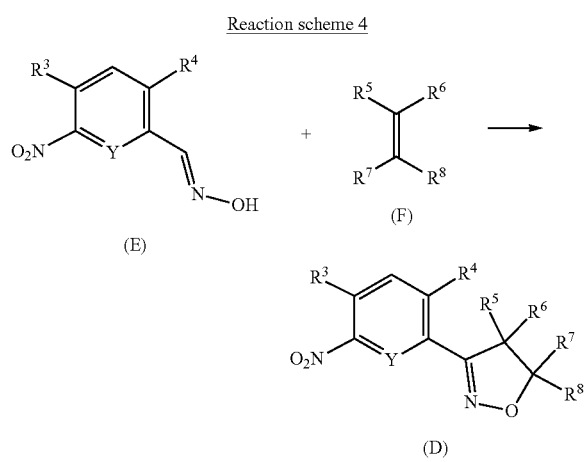

For example, an oxime of formula (E) may be treated with N-chlorosuccinimide in a suitable solvent, such as dimethylformamide, and the resulting intermediate then treated with an alkene of formula (F) in the presence of a base, such as triethylamine, in a suitable solvent such as dichloromethane.

Alkenes of formula (F) are available or may be prepared by methods well known in the literature.

Oximes of formula (E) may be prepared from aldehydes of formula (G) as shown in reaction scheme 5

Reaction scheme 5

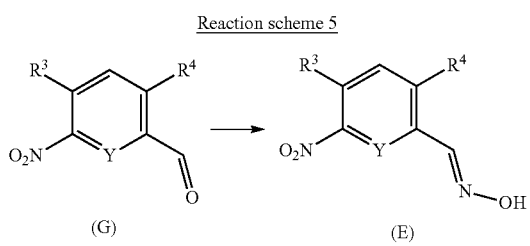

For example, an aldehyde of formula (G) may be treated with hydroxylamine hydrochloride in a suitable solvent, such as a mixture of water and ethanol.

Aldehydes of formula (G) are available or can be prepared by methods known in the literature.

Compounds of formula (I-A), which are compounds of formula (I) in which $R^7$ is a carboxylic acid group, may be prepared from compounds of formula (I-B), which are compounds of formula (I) in which $R^7$ is $CO_2R^9$, as shown in reaction scheme 6.

Reaction scheme 6

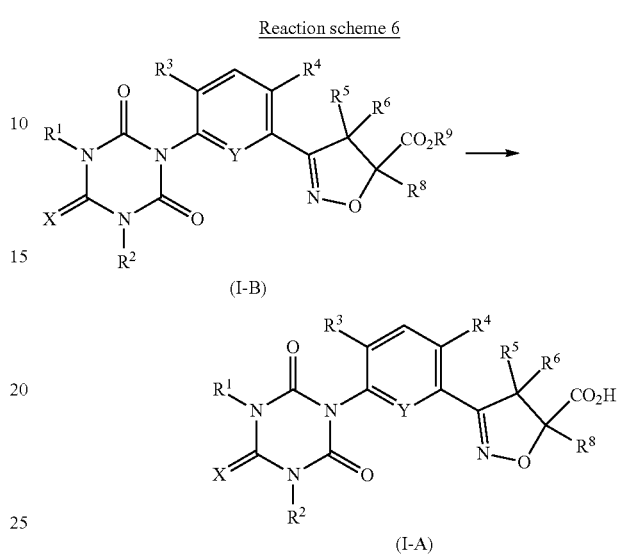

For example, a compound of formula (I-B) may be treated with sodium hydroxide in a suitable solvent, such as a mixture of water and ethanol.

Compounds of formula (I-C), which are compounds of formula (I) in which $R^7$ is a hydroxymethyl group, may be prepared from compounds of formula (I-A or I-B), as shown in reaction scheme 7.

Reaction scheme 7

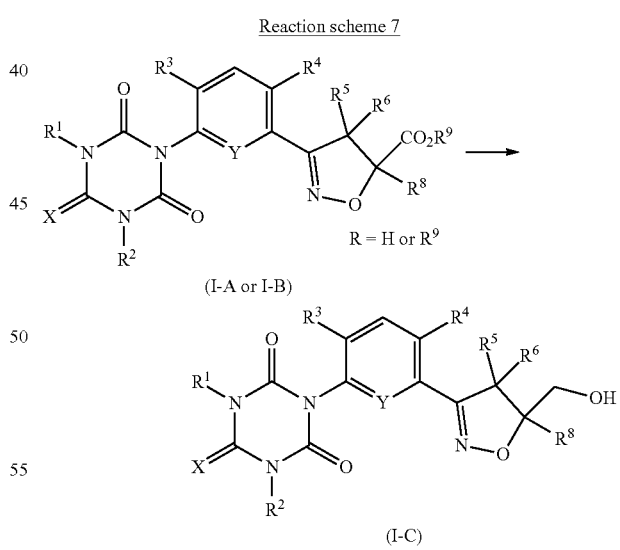

For example, a compound of formula (I-A) or (I-B) may be treated with a suitable reducing agent, for example a metal hydride reagent, such as sodium borohydride or borane, in a suitable solvent, such as tetrahydrofuran.

Compounds of formula (I-D), which are compounds of formula (I) in which $R^7$ is $CH_2OR^{12}$, may be prepared from compounds of formula (I-C) as shown in reaction scheme 8.

Reaction scheme 8

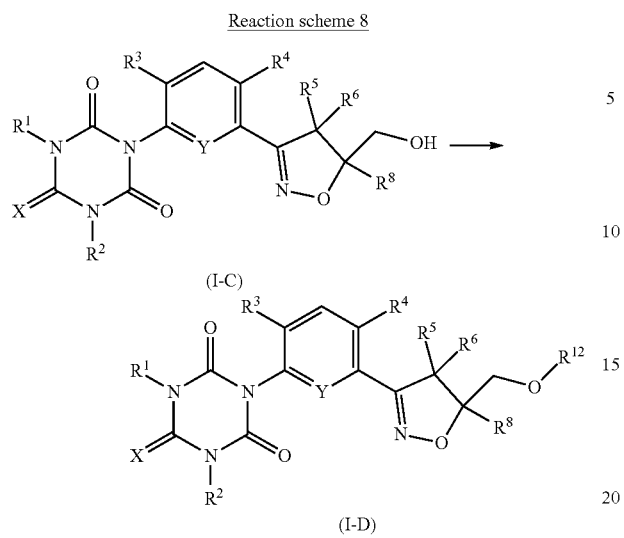

For example, a compound of formula (I-C) may be treated with a reagent $R^{12}$-LG, wherein LG is a leaving group such as a halogen, such as an alkylating agent, acylating agent or sulfonylating agent, in the presence of a base, such as sodium hydride or triethylamine, in a suitable solvent, such as tetrahydrofuran.

Compounds of formula (I-E), which are compounds of formula (I) in which $R^7$ is $CONR^{10}R^{11}$, may be prepared from compounds of formula (I-A) as shown in reaction scheme 9.

Reaction scheme 9

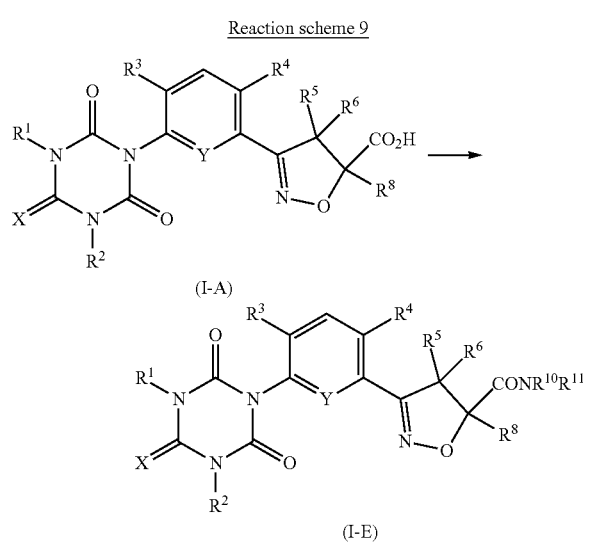

For example, a compound of formula (I-A) may be treated with a halogenating reagent, such as oxalyl chloride, in a suitable solvent, such as dichloromethane, to form an acyl halide which may be treated with a reagent $HNR^{10}R^{11}$ in the presence of a base, such as triethylamine, in a suitable solvent, such as dichloromethane.

Compounds of formula (I-G), which are compounds of formula (I) in which $R^7$ is an oxime group, may be prepared from compounds of formula (I-F), which are compounds of formula (I) in which $R^7$ is a ketone group, as shown in reaction scheme 10.

Reaction scheme 10

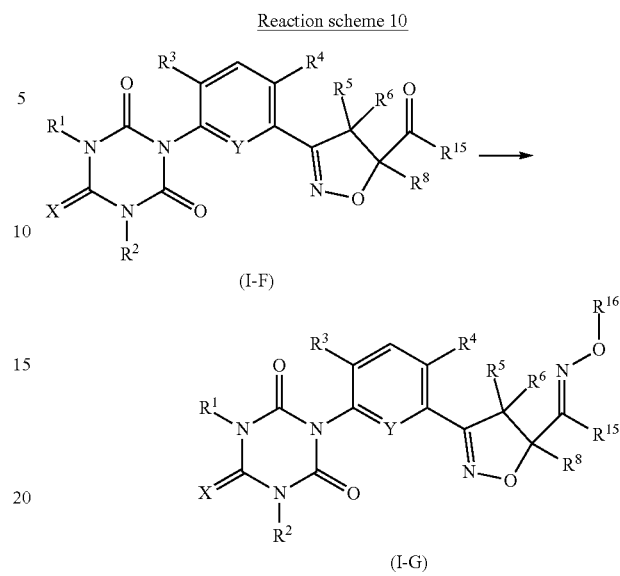

For example, a compound of formula (I-F) may be treated a hydroxylamine $H_2NOR^{16}$, or a salt thereof, optionally in the presence of a base, such as triethylamine, in a suitable solvent, such as ethanol.

Compounds of formula (I-H), which are compounds of formula (I) in which $R^7$ is a hydrazone group, may be prepared from compounds of formula (I-F), which are compounds of formula (I) in which $R^7$ is a ketone group, as shown in reaction scheme 11.

Reaction scheme 11

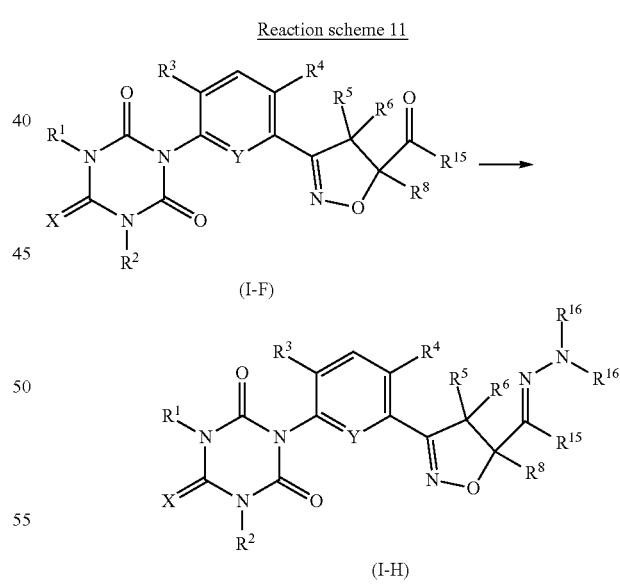

For example, a compound of formula (I-F) may be treated a hydrazine $H_2NN(R^{16})_2$, or a salt thereof, optionally in the presence of a base, such as triethylamine, in a suitable solvent, such as ethanol.

One skilled in the art will realise that it is often possible to alter the order in which the transformations described above are conducted, or to combine them in alternative ways to prepare a wide range of compounds of formula (I).

Multiple steps may also be combined in a single reaction. All such variations are contemplated within the scope of the invention.

The skilled person will also be aware that some reagents will be incompatible with certain values or combinations of the substituents X, Y, Z, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ as defined herein, and any additional steps, such as protection and/or deprotection steps, which are necessary to achieve the desired transformation will be clear to the skilled person.

The compounds according to the invention can be used as herbicidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). For water-soluble compounds, soluble liquids, water-soluble concentrates or water soluble granules are preferred. Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, takeup enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
 active ingredient: 1 to 95%, preferably 60 to 90%
 surface-active agent: 1 to 30%, preferably 5 to 20%
 liquid carrier: 1 to 80%, preferably 1 to 35%
Dusts:
 active ingredient: 0.1 to 10%, preferably 0.1 to 5%
 solid carrier: 99.9 to 90%, preferably 99.9 to 99%
Suspension Concentrates:
 active ingredient: 5 to 75%, preferably 10 to 50%
 water: 94 to 24%, preferably 88 to 30%
 surface-active agent: 1 to 40%, preferably 2 to 30%
Wettable Powders:
 active ingredient: 0.5 to 90%, preferably 1 to 80%
 surface-active agent: 0.5 to 20%, preferably 1 to 15%
 solid carrier: 5 to 95%, preferably 15 to 90%
Granules:
 active ingredient: 0.1 to 30%, preferably 0.1 to 15%
 solid carrier: 99.5 to 70%, preferably 97 to 85%

The composition of the present may further comprise at least one additional pesticide. For example, the compounds according to the invention can also be used in combination with other herbicides or plant growth regulators. In a preferred embodiment the additional pesticide is a herbicide and/or herbicide safener.

Thus, compounds of formula (I) can be used in combination with one or more other herbicides to provide various herbicidal mixtures. Specific examples of such mixtures include (wherein "I" represents a compound of formula (I)):—I+acetochlor; I+acifluorfen (including acifluorfen-sodium); I+aclonifen; I+alachlor; I+alloxydim; I+ametryn; I+amicarbazone; I+amidosulfuron; I+aminocyclopyrachlor; I+aminopyralid; I+amitrole; I+asulam; I+atrazine; I+bensulfuron (including bensulfuron-methyl); I+bentazone; I+bicyclopyrone; I+bilanafos; I+bifenox; I+bispyribac-sodium; I+bixlozone; I+bromacil; I+bromoxynil; I+butachlor; I+butafenacil; I+cafenstrole; I+carfentrazone (including carfentrazone-ethyl); cloransulam (including cloransulam-methyl); I+chlorimuron (including chlorimuron-ethyl); I+chlorotoluron; I+cinosulfuron; I+chlorsulfuron; I+cinmethylin; I+clacyfos; I+clethodim; I+clodinafop (including clodinafop-propargyl); I+clomazone; I+clopyralid; I+cyclopyranil; I+cyclopyrimorate; I+cyclosulfamuron; I+cyhalofop (including cyhalofop-butyl); I+2,4-D (including the choline salt and 2-ethylhexyl ester thereof); I+2,4-DB; I+daimuron; I+desmedipham; I+dicamba (including the aluminum, aminopropyl, bis-aminopropylmethyl, choline, dichloroprop, diglycolamine, dimethylamine, dimethylammonium, potassium and sodium salts thereof); I+diclofop-methyl; I+diclosulam; I+diflufenican; I+difenzoquat; I+diflufenican; I+diflufenzopyr; I+dimethachlor; I+dimethenamid-P; I+diquat dibromide; I+diuron; I+esprocarb; I+ethalfluralin; I+ethofumesate; I+fenoxaprop (including fenoxaprop-P-ethyl); I+fenoxasulfone; I+fenquinotrione; I+fentrazamide; I+flazasulfuron; I+florasulam; I+florpyrauxifen; I+fluazifop (including fluazifop-P-butyl); I+flucarbazone (including flucarbazone-sodium); I+flufenacet; I+flumetralin; I+flumetsulam; I+flumioxazin; I+flupyrsulfuron (including flupyrsulfuron-methyl-sodium); I+fluroxypyr (including fluroxypyr-meptyl); I+fluthiacet-methyl; I+fomesafen; I+foramsulfuron; I+glufosinate (including the ammonium salt thereof); I+glyphosate (including the diammonium, isopropylammonium and potassium salts thereof); I+halauxifen (including halauxifen-methyl); I+halosulfuron-methyl; I+haloxyfop (including haloxyfop-methyl); I+hexazinone; I+hydantocidin; I+imazamox; I+imazapic; I+imazapyr; I+imazaquin; I+imazethapyr; I+indaziflam; I+iodosulfuron (including iodosulfuron-methyl-sodium); I+iofensulfuron; I+iofensulfuron-sodium; I+ioxynil; I+ipfencarbazone; I+isoproturon; I+isoxaben; I+isoxaflutole; I+lactofen; I+lancotrione; I+linuron; I+MCPA; I+MCPB; I+mecoprop-P; I+mefenacet; I+mesosulfuron; I+mesosulfuron-methyl; I+mesotrione; I+metamitron; I+metazachlor; I+methiozolin; I+metobromuron; I+metolachlor; I+metosulam; I+metoxuron; I+metribuzin; I+metsulfuron; I+molinate; I+napropamide; I+nicosulfuron; I+norflurazon; I+orthosulfamuron; I+oxadiargyl; I+oxadiazon; I+oxasulfuron; I+oxyfluorfen; I+paraquat dichloride; I+pendimethalin; I+penoxsulam; I+phenmedipham; I+picloram; I+picolinafen; I+pinoxaden; I+pretilachlor; I+primisulfuron-methyl; I+prodiamine; I+prometryn; I+propachlor; I+propanil; I+propaquizafop; I+propham; I+propyrisulfuron, I+propyzamide; I+prosulfocarb; I+prosulfuron; I+pyraclonil; I+pyraflufen (including pyraflufen-ethyl): I+pyrasulfotole; I+pyrazolynate, I+pyrazosulfuron-ethyl; I+pyribenzoxim; I+pyridate; I+pyriftalid; I+pyrimisulfan, I+pyrithiobac-sodium; I+pyroxasulfone; I+pyroxsulam; I+quinclorac; I+quinmerac; I+quizalofop (including quizalofop-P-ethyl and quizalofop-P-tefuryl);

I+rimsulfuron; I+saflufenacil; I+sethoxydim; I+simazine; I+S-metolachlor; I+sulcotrione; I+sulfentrazone; I+sulfosulfuron; I+tebuthiuron; I+tefuryltrione; I+tembotrione; I+terbuthylazine; I+terbutryn; I+thiencarbazone; I+thifensulfuron; I+tiafenacil; I+tolpyralate; I+topramezone; I+tralkoxydim; I+triafamone; I+triallate; I+triasulfuron; I+tribenuron (including tribenuron-methyl); I+triclopyr; I+trifloxysulfuron (including trifloxysulfuron-sodium); I+trifludimoxazin; I+trifluralin; I+triflusulfuron; I+tritosulfuron; I+4-hydroxy-1-methoxy-5-methyl-3-[4-(trifluoromethyl)-2-pyridyl]imidazolidin-2-one; I+4-hydroxy-1,5-dimethyl-3-[4-(trifluoromethyl)-2-pyridyl]imidazolidin-2-one; I+5-ethoxy-4-hydroxy-1-methyl-3-[4-(trifluoromethyl)-2-pyridyl]imidazolidin-2-one; I+4-hydroxy-1-methyl-3-[4-(trifluoromethyl)-2-pyridyl]imidazolidin-2-one; I+4-hydroxy-1,5-dimethyl-3-[1-methyl-5-(trifluoromethyl) pyrazol-3-yl]imidazolidin-2-one; I+(4R)1-(5-tert-butylisoxazol-3-yl)-4-ethoxy-5-hydroxy-3-methyl-imidazolidin-2-one; I+3-[2-(3,4-dimethoxyphenyl)-6-methyl-3-oxo-pyridazine-4-carbonyl]bicyclo[3.2.1]octane-2,4-dione; I+2-[2-(3,4-dimethoxyphenyl)-6-methyl-3-oxo-pyridazine-4-carbonyl]-5-methyl-cyclohexane-1,3-dione; I+2-[2-(3,4-dimethoxyphenyl)-6-methyl-3-oxo-pyridazine-4-carbonyl]cyclohexane-1,3-dione; I+2-[2-(3,4-dimethoxyphenyl)-6-methyl-3-oxo-pyridazine-4-carbonyl]-5,5-dimethyl-cyclohexane-1,3-dione; I+6-[2-(3,4-dimethoxyphenyl)-6-methyl-3-oxo-pyridazine-4-carbonyl]-2,2,4,4-tetramethyl-cyclohexane-1,3,5-trione; I+2-[2-(3,4-dimethoxyphenyl)-6-methyl-3-oxo-pyridazine-4-carbonyl]-5-ethyl-cyclohexane-1,3-dione; I+2-[2-(3,4-dimethoxyphenyl)-6-methyl-3-oxo-pyridazine-4-carbonyl]-4,4,6,6-tetramethyl-cyclohexane-1,3-dione; I+2-[6-cyclopropyl-2-(3,4-dimethoxyphenyl)-3-oxo-pyridazine-4-carbonyl]-5-methyl-cyclohexane-1,3-dione; I+3-[6 cyclopropyl-2-(3,4-dimethoxyphenyl)-3-oxo-pyridazine-4-carbonyl]bicyclo[3.2.1]octane-2,4-dione; I+2-[6-cyclopropyl-2-(3,4-dimethoxyphenyl)-3-oxo-pyridazine-4-carbonyl]-5,5-dimethyl-cyclohexane-1,3-dione; I+6-[6-cyclopropyl-2-(3,4-dimethoxyphenyl)-3-oxo-pyridazine-4-carbonyl]-2,2,4,4-tetramethyl-cyclohexane-1,3,5-trione; I+2-[6-cyclopropyl-2-(3,4-dimethoxyphenyl)-3-oxo-pyridazine-4-carbonyl]cyclohexane-1,3-dione; I+4-[2-(3,4-dimethoxyphenyl)-6-methyl-3-oxo-pyridazine-4-carbonyl]-2,2,6,6-tetramethyl-tetrahydropyran-3,5-dione and I+4-[6-cyclopropyl-2-(3,4-dimethoxyphenyl)-3-oxo-pyridazine-4-carbonyl]-2,2,6,6-tetramethyl-tetrahydropyran-3,5-dione.

The mixing partners of the compound of formula (I) may also be in the form of esters or salts, as mentioned e.g. in The Pesticide Manual, Fourteenth Edition, British Crop Protection Council, 2006.

The compound of formula (I) can also be used in mixtures with other agrochemicals such as fungicides, nematicides or insecticides, examples of which are given in The Pesticide Manual.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

Compounds of formula (I) of the present invention may also be combined with herbicide safeners. Preferred combinations (wherein "I" represents a compound of formula (I)) include:—I+benoxacor, I+cloquintocet (including cloquintocet-mexyl); I+cyprosulfamide; I+dichlormid; I+fenchlorazole (including fenchlorazole-ethyl); 1+fenclorim; I+fluxofenim; 1+furilazole 1+isoxadifen (including isoxadifen-ethyl); I+mefenpyr (including mefenpyr-diethyl); I+metcamifen; I+N-(2-methoxybenzoyl)-4-[(methylaminocarbonyl)amino] benzenesulfonamide and I+oxabetrinil.

Particularly preferred are mixtures of a compound of formula (I) with cyprosulfamide, isoxadifen (including isoxadifen-ethyl), cloquintocet (including cloquintocet-mexyl) and/or N-(2-methoxybenzoyl)-4-[(methyl-aminocarbonyl)amino]benzenesulfonamide.

The safeners of the compound of formula (I) may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of formula (I) to safener is from 100:1 to 1:10, especially from 20:1 to 1:1.

The mixtures can advantageously be used in the above-mentioned formulations (in which case "active ingredient" relates to the respective mixture of compound of formula (I) with the safener).

The compounds of formula (I) of this invention are useful as herbicides. The present invention therefore further comprises a method for controlling unwanted plants comprising applying to the said plants or a locus comprising them, an effective amount of a compound of the invention or a herbicidal composition containing said compound. 'Controlling' means killing, reducing or retarding growth or preventing or reducing germination. Generally the plants to be controlled are unwanted plants (weeds). 'Locus' means the area in which the plants are growing or will grow.

The rates of application of compounds of formula (I) may vary within wide limits and depend on the nature of the soil, the method of application (pre-emergence; post-emergence; application to the seed furrow; no tillage application etc.), the crop plant, the weed(s) to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha. A preferred range is 10-200 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are Knockout® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

Compounds of formula (I) and compositions of the invention can typically be used to control a wide variety of monocotyledonous and dicotyledonous weed species. Examples of monocotyledonous species that can typically be controlled include *Alopecurus myosuroides, Avena fatua, Brachiaria plantaginea, Bromus tectorum, Cyperus esculentus, Digitaria sanguinalis, Echinochloa crus-galli, Lolium perenne, Lolium multiflorum, Panicum miliaceum, Poa annua, Setaria viridis, Setaria faberi* and *Sorghum bicolor*. Examples of dicotyledonous species that can be controlled include *Abutilon theophrasti, Amaranthus retroflexus, Bidens pilosa, Chenopodium album, Euphorbia heterophylla, Galium aparine, Ipomoea hederacea, Kochia scoparia, Polygonum convolvulus, Sida spinosa, Sinapis arvensis, Solanum nigrum, Stellaria media, Veronica persica* and *Xanthium strumarium*.

The compounds of formula (I) are also useful for pre-harvest desiccation in crops, for example, but not limited to, potatoes, soybean, sunflowers and cotton. Pre-harvest desiccation is used to desiccate crop foliage without significant damage to the crop itself to aid harvesting.

Compounds/compositions of the invention are particularly useful in non-selective burn-down applications, and as such may also be used to control volunteer or escape crop plants.

Various aspects and embodiments of the present invention will now be illustrated in more detail by way of example. It will be appreciated that modification of detail may be made without departing from the scope of the invention.

EXAMPLES

The Examples which follow serve to illustrate, but do not limit, the invention.

Synthesis Examples

Example 1 Synthesis of Ethyl 3-[2-chloro-5-(3,5-dimethyl-2,6-dioxo-4-thioxo-1,3,5-triazinan-1-yl)-4-fluoro-phenyl]-5-methyl-4H-isoxazole-5-carboxylate (Compound 47)

Step 1 Synthesis of 2-chloro-4-fluoro-5-nitro-benzaldehyde Oxime

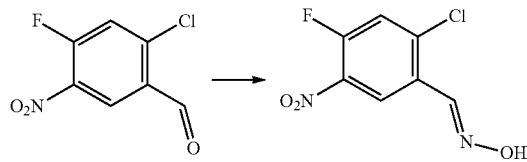 [SMILES: O=Cc1cc([N+](=O)[O-])c(F)cc1Cl ; O=[N+]([O-])c1cc(/C=N/O)c(Cl)cc1F]

Hydroxylamine hydrochloride (6.39 g, 92 mmol) was added to a stirred solution of 2-chloro-4-fluoro-5-nitro-benzaldehyde (13 g, 61.3 mmol) in ethanol (65 ml) at room temperature. The resulting solution was stirred at room temperature for a further 60 mins. Water (125 ml) was added and the resulting mixture filtered to provide 2-chloro-4-fluoro-5-nitro-benzaldehyde oxime as a yellow solid (13.0 g).

$^1$H NMR (400 MHz, CHCl$_3$) δ 8.65 (d, 1H), 8.5 (s, 1H), 8.1 (brs, 1H), 7.4 (d, 1H) ppm.

Also prepared by this general method were:
2-Chloro-5-nitro-benzaldehyde oxime
$^1$H NMR (400 MHz, CHCl$_3$) δ 8.75 (s, 1H), 8.55 (s, 1H), 8.15 (m, 1H), 7.9 (s, 1H), 7.6 (m, 1H) ppm.
2,4-Dichloro-5-nitro-benzaldehyde oxime Step 2 Synthesis of ethyl 3-(2-chloro-4-fluoro-5-nitro-phenyl)-5-methyl-4H-isoxazole-5-carboxylate

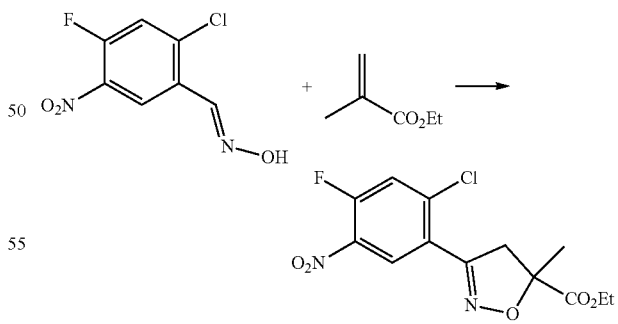

1-Chloropyrrolidine-2,5-dione (0.6 ml, 6.6 mmol) was added portion wise over 10 mins to a stirred solution of 2-chloro-4-fluoro-5-nitro-benzaldehyde oxime (1.2 g, 5.5 mmol) in N,N-dimethylformamide (4.8 ml) at 30° C. The resulting mixture was stirred at 35° C. for 1 hour, then cooled to room temperature and dichloromethane (50 ml) added. The mixture was washed with dilute hydrochloric acid (15 ml), dried and cooled to 5° C. To this stirred solution was added dropwise a mixture of triethylamine (1.33 ml 9.5 mmol) and ethyl 2-methylprop-2-enoate (1.14 g, 9.5 mmol). After standing at room temperature for 17 hours, dilute hydrochloric acid (5 ml) was added, the phases separated and the organic dried and purified by chromatography to provide ethyl 3-(2-chloro-4-fluoro-5-nitro-phenyl)-5-methyl-4H-isoxazole-5-carboxylate (1.0 g).

$^1$H NMR (400 MHz, CHCl$_3$) δ 8.45 (d, 1H), 7.45 (d, 1H), 4.3 (q, 2H), 4.0 (d, 1H), 3.4 (d, 1H), 1.75 (s, 3H), 1.35 (t, 3H) ppm.

Also prepared by this general method were:
Ethyl 3-(2-chloro-5-nitro-phenyl)-5-methyl-4H-isoxazole-5-carboxylate
$^1$H NMR (400 MHz, CHCl$_3$) δ 8.55 (d, 1H), 8.2 (d, 1H), 7.65 (d, 1H), 4.3 (q, 2H), 4.05 (d, 1H), 3.4 (d, 1H), 1.75 (s, 3H), 1.35 (t, 3H) ppm.

Methyl 3-(2-chloro-4-fluoro-5-nitro-phenyl)-5-(trifluoromethyl)-4H-isoxazole-5-carboxylate
$^1$H NMR (400 MHz, CHCl$_3$) δ 8.45 (d, 1H), 7.45 (d, 1H), 4.2 (d, 1H), 3.95 (d, 1H), 3.95 (s, 3H) ppm.

Methyl 3-(2-chloro-4-fluoro-5-nitro-phenyl)-4,5-dimethyl-4H-isoxazole-5-carboxylate
$^1$H NMR (400 MHz, CHCl$_3$) δ 8.3 (d, 1H), 7.45 (d, 1H), 3.9 (q, 1H), 3.8 (s, 3H), 1.75 (s, 3H), 1.1 (d, 3H) ppm.

[3-(2-Chloro-4-fluoro-5-nitro-phenyl)-5-methyl-4H-isoxazol-5-yl]methanol
$^1$H NMR (400 MHz, CHCl$_3$) δ 8.45 (d, 1H), 7.45 (d, 1H), 3.8 (br d, 1H), 3.65 (d, 1H), 3.6 (br d, 1H), 3.2 (d, 1H), 2.1 (m, 1H), 1.5 (s, 3H) ppm.

1-[3-(2-Chloro-4-fluoro-5-nitro-phenyl)-5-methyl-4H-isoxazol-5-yl]ethanone
$^1$H NMR (400 MHz, CHCl$_3$) δ 8.4 (d, 1H), 7.45 (d, 1H), 3.95 (d, 1H), 3.2 (d, 1H), 2.35 (s, 3H), 1.65 (s, 3H) ppm.

Ethyl 3-(2,4-dichloro-5-nitro-phenyl)-5-methyl-4H-isoxazole-5-carboxylate
$^1$H NMR (400 MHz, CHCl$_3$) δ 8.35 (s, 1H), 7.7 (s, 1H), 4.3 (q, 2H), 4.05 (d, 1H), 3.4 (d, 1H), 1.75 (s, 3H), 1.35 (t, 3H) ppm.

Methyl 3-(2-chloro-4-fluoro-5-nitro-phenyl)-5-methoxy-4H-isoxazole-5-carboxylate
$^1$H NMR (400 MHz, CHCl$_3$) δ 8.55 (d, 1H), 7.45 (d, 1H), 4.0 (d, 1H), 3.9 (s, 3H), 3.6 (d, 1H), 3.5 (s, 3H) ppm.

Step 3 Synthesis of ethyl 3-(5-amino-2-chloro-4-fluoro-phenyl)-5-methyl-4H-isoxazole-5-carboxylate

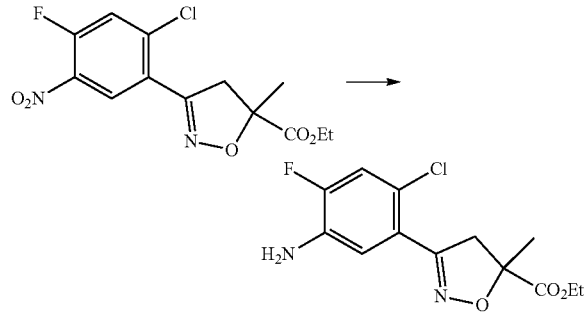

Tin dichloride hydrate (2.3 g, 12.1 mmol) was added to a stirred solution of ethyl 3-(2-chloro-4-fluoro-5-nitro-phenyl)-5-methyl-4H-isoxazole-5-carboxylate (1.0 g, 3.0 mmol) in ethyl acetate (60 ml) at room temperature. After 5 minutes the mixture was heated at reflux for 3 hours, cooled and evaporated under reduced pressure to provide a brown oil, which was purified by chromatography to provide ethyl 3-(5-amino-2-chloro-4-fluoro-phenyl)-5-methyl-4H-isoxazole-5-carboxylate (800 mg).

$^1$H NMR (400 MHz, CHCl$_3$) δ 7.15 (d, 1H), 7.05 (d, 1H), 4.3 (q, 2H), 3.95 (d, 1H), 3.4 (d, 1H), 1.7 (s, 3H), 1.3 (t, 3H) ppm (NH$_2$ not observed).

Also prepared by this general method were:
Ethyl 3-(5-amino-2-chloro-phenyl)-5-methyl-4H-isoxazole-5-carboxylate.

Methyl 3-(5-amino-2-chloro-4-fluoro-phenyl)-5-(trifluoromethyl)-4H-isoxazole-5-carboxylate
$^1$H NMR (400 MHz, CHCl$_3$) δ 7.15 (d, 1H), 7.1 (d, 1H), 4.2 (d, 1H), 3.95 (d, 1H), 3.9 (s, 3H), 3.85 (br s, 2H) ppm.

Methyl 3-(5-amino-2-chloro-4-fluoro-phenyl)-4,5-dimethyl-4H-isoxazole-5-carboxylate
$^1$H NMR (400 MHz, CHCl$_3$) δ 7.15 (d, 1H), 6.9 (d, 1H), 3.9 (q, 1H), 3.85 (br s, 2H), 3.8 (s, 3H), 1.75 (s, 3H), 1.0 (d, 3H) ppm.

[3-(5-Amino-2-chloro-4-fluoro-phenyl)-5-methyl-4H-isoxazol-5-yl]methyl acetate.

1-[3-(5-Amino-2-chloro-4-fluoro-phenyl)-5-methyl-4H-isoxazol-5-yl]ethanone.

Ethyl 3-(5-amino-2,4-dichloro-phenyl)-5-methyl-4H-isoxazole-5-carboxylate
$^1$H NMR (400 MHz, CHCl$_3$) δ 7.35 (s, 1H), 7.3 (s, 1H), 4.3 (q, 2H), 4.1 (br s, 2H), 3.95 (d, 1H), 3.4 (d, 1H), 1.75 (s, 3H), 1.35 (t, 3H) ppm.

Methyl 3-(5-amino-2-chloro-4-fluoro-phenyl)-5-methoxy-4H-isoxazole-5-carboxylate
$^1$H NMR (400 MHz, CHCl$_3$) δ 7.15 (d, 1H), 7.1 (d, 1H), 3.95 (d, 1H), 3.9 (s, 3H), 3.85 (brs, 2H), 3.6 (d, 1H), 3.45 (s, 3H) ppm.

Step 4 Synthesis of ethyl 3-(2-chloro-4-fluoro-5-isocyanato-phenyl)-5-methyl-4H-isoxazole-5-carboxylate

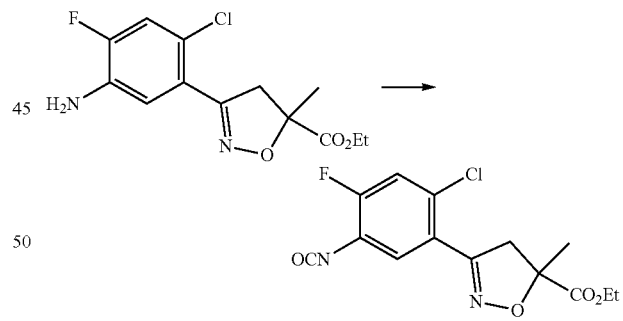

A solution of ethyl 3-(5-amino-2-chloro-4-fluoro-phenyl)-5-methyl-4H-isoxazole-5-carboxylate (800 mg, 2.66 mmol) in dry toluene (16 ml) was added to stirred diphosgene (0.4 ml, 3.2 mmol) at room temperature and the mixture then heated at reflux for 3 hours, cooled and evaporated under reduced pressure. Toluene (10 ml) was added and the mixture evaporated under reduced pressure to provide ethyl 3-(2-chloro-4-fluoro-5-isocyanato-phenyl)-5-methyl-4H-isoxazole-5-carboxylate as a light brown liquid (750 mg).

$^1$H NMR (400 MHz, CHCl$_3$) δ 7.45 (d, 1H), 7.25 (d, 1H), 4.3 (q, 2H), 3.9 (d, 1H), 3.35 (d, 1H), 1.75 (s, 3H), 1.35 (t, 3H) ppm.

Also prepared by this general method were:
Ethyl 3-(2-chloro-5-isocyanato-phenyl)-5-methyl-4H-isoxazole-5-carboxylate.
Methyl 3-(2-chloro-4-fluoro-5-isocyanato-phenyl)-5-(trifluoromethyl)-4H-isoxazole-5-carboxylate.
$^1$H NMR (400 MHz, CHCl$_3$) δ 7.45 (d, 1H), 7.3 (d, 1H), 4.15 (d, 1H), 3.95 (d, 1H), 3.95 (s, 3H) ppm.
Methyl 3-(2-chloro-4-fluoro-5-isocyanato-phenyl)-4,5-dimethyl-4H-isoxazole-5-carboxylate.
1-[3-(2-Chloro-4-fluoro-5-isocyanato-phenyl)-5-methyl-4H-isoxazol-5-yl]methyl acetate.
1-[3-(2-chloro-4-fluoro-5-isocyanato-phenyl)-5-methyl-4H-isoxazol-5-yl]ethanone.
Ethyl 3-(2,4-dichloro-5-isocyanato-phenyl)-5-methyl-4H-isoxazole-5-carboxylate.
Methyl 3-(2-chloro-4-fluoro-5-isocyanato-phenyl)-5-methoxy-4H-isoxazole-5-carboxylate
$^1$H NMR (400 MHz, CHCl$_3$) δ 7.5 (d, 1H), 7.25 (d, 1H), 3.95 (d, 1H), 3.9 (s, 3H), 3.6 (d, 1H), 3.5 (s, 3H) ppm.

Step 5 Preparation of ethyl 3-[2-chloro-5-(3,5-dimethyl-2,6-dioxo-4-thioxo-1,3,5-triazinan-1-yl)-4-fluoro-phenyl]-5-methyl-4H-isoxazole-5-carboxylate (Compound 47)

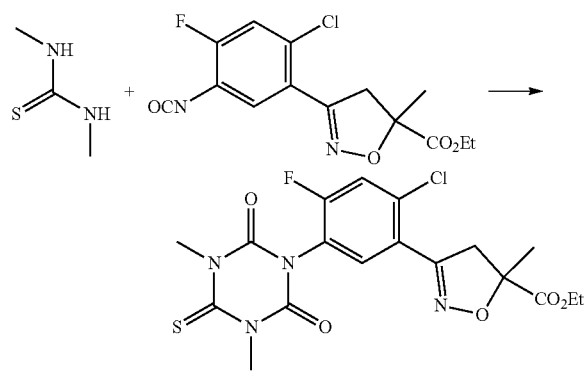

A solution of 1,3-dimethylthiourea (0.31 g, 2.94 mmol) and triethylamine (0.45 ml, 3.82 mmol) in toluene was added to a stirred solution of ethyl 3-(2-chloro-4-fluoro-5-isocyanato-phenyl)-5-methyl-4H-isoxazole-5-carboxylate (800 mg, 2.45 mmol) in toluene (16 ml) at room temperature. The resulting mixture was heated to reflux and carbonyldiimidazole (0.62 g, 3.67 mmol) added portionwise over 15 minutes. The mixture was heated at reflux for 3.5 hours, cooled and evaporated under reduced pressure to give a brown oil which was purified by chromatography to provide ethyl 3-[2-chloro-5-(3,5-dimethyl-2,6-dioxo-4-thioxo-1,3,5-triazinan-1-yl)-4-fluoro-phenyl]-5-methyl-4H-isoxazole-5-carboxylate (Compound 47) (775 mg).
$^1$H NMR (400 MHz, CHCl$_3$) δ 7.75 (d, 1H), 7.35 (d, 1H), 4.25 (q, 2H), 4.0 (d, 1H), 3.75 (s, 6H), 3.4 (d, 1H), 1.7 (s, 3H), 1.3 (t, 3H) ppm.
The individual enantiomers of Compound 47 were prepared by chiral chromatography ($^1$H NMR as above).
Also prepared by this general method were:
Ethyl 3-[2-chloro-5-(3,5-dimethyl-2,6-dioxo-4-thioxo-1,3,5-triazinan-1-yl)phenyl]-5-methyl-4H-isoxazole-5-carboxylate (Compound 36)
$^1$H NMR (400 MHz, CHCl$_3$) δ 7.7 (d, 1H), 7.55 (d, 1H), 7.25 (m, 1H), 4.25 (q, 2H), 4.0 (d, 1H), 3.75 (s, 6H), 3.4 (d, 1H), 1.7 (s, 3H), 1.3 (t, 3H) ppm.

Methyl 3-[2-chloro-5-(3,5-dimethyl-2,6-dioxo-4-thioxo-1,3,5-triazinan-1-yl)-4-fluoro-phenyl]-5-trifluoromethyl-4H-isoxazole-5-carboxylate (Compound 262)
$^1$H NMR (400 MHz, CHCl$_3$) δ 7.8 (d, 1H), 7.45 (d, 1H), 4.2 (d, 1H), 4.0 (d, 1H), 3.95 (s, 3H), 3.8 (s, 6H), ppm.
Methyl 3-[2-chloro-5-(3,5-dimethyl-2,6-dioxo-4-thioxo-1,3,5-triazinan-1-yl)-4-fluoro-phenyl]-4,5-dimethyl-4H-isoxazole-5-carboxylate (Compound 145)
$^1$H NMR (400 MHz, CHCl$_3$) δ 7.5 (d, 1H), 7.4 (d, 1H), 3.95 (q, 1H), 3.8 (s, 3H), 3.75 (s, 6H), 1.75 (s, 3H), 1.1 (d, 3H) ppm.
[3-[2-Chloro-5-(3,5-dimethyl-2,6-dioxo-4-thioxo-1,3,5-triazinan-1-yl)-4-fluoro-phenyl]-5-methyl-4H-isoxazol-5-yl]methyl acetate (Compound 51)
$^1$H NMR (400 MHz, CHCl$_3$) δ 7.75 (d, 1H), 7.35 (d, 1H), 4.2 (q, 2H), 3.75 (s, 6H), 3.5 (d, 1H), 3.25 (d, 1H), 2.1 (s, 3H), 1.5 (s, 3H) ppm.
3-[5-(5-Acetyl-5-methyl-4H-isoxazol-3-yl)-4-chloro-2-fluoro-phenyl]-1,5-dimethyl-6-thioxo-1,3,5-triazinane-2,4-dione (Compound 290)
$^1$H NMR (400 MHz, CHCl$_3$) δ 7.7 (d, 1H), 7.4 (d, 1H), 3.95 (d, 1H), 3.75 (s, 6H), 3.2 (d, 1H), 2.35 (s, 3H), 1.55 (s, 3H) ppm.
Ethyl 3-[2,4-dichloro-5-(3,5-dimethyl-2,6-dioxo-4-thioxo-1,3,5-triazinan-1-yl)phenyl]-5-methyl-4H-isoxazole-5-carboxylate (Compound 58)
$^1$H NMR (400 MHz, CHCl$_3$) δ 7.8 (s, 1H), 7.65 (s, 1H), 4.4 (q, 2H), 4.0 (d, 1H), 3.75 (s, 6H), 3.4 (d, 1H), 1.7 (s, 3H), 1.3 (t, 3H) ppm.
Methyl 3-[2-chloro-5-(3,5-dimethyl-2,6-dioxo-4-thioxo-1,3,5-triazinan-1-yl)-4-fluoro-phenyl]-5-methoxy-4H-isoxazole-5-carboxylate (Compound 311)
$^1$H NMR (400 MHz, CHCl$_3$) δ 7.8 (d, 1H), 7.4 (d, 1H), 3.95 (d, 1H), 3.9 (s, 3H), 3.8 (s, 6H), 3.6 (d, 1H), 3.45 (s, 3H) ppm.

Example 2 Preparation of 3-[2-chloro-5-(3,5-dimethyl-2,6-dioxo-4-thioxo-1,3,5-triazinan-1-yl)-4-fluoro-phenyl]-5-methyl-4H-isoxazole-5-carboxylic Acid (Compound 45)

Step 1 Preparation of 3-[2-chloro-4-fluoro-5-[[methyl(methylcarbamothioyl)carbamoyl]amino]phenyl]-5-methyl-4H-isoxazole-5-carboxylic Acid

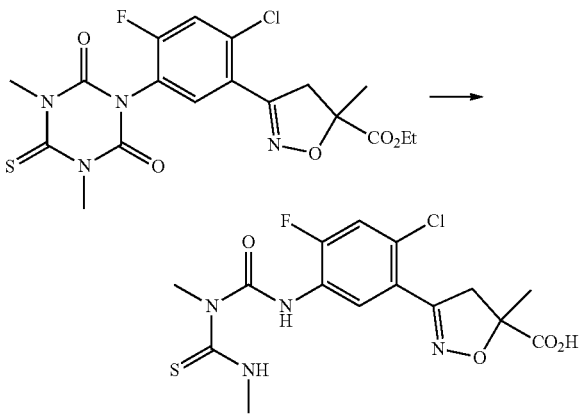

Aqueous sodium hydroxide (2N; 0.87 ml, 1.75 mmol) was added to a stirred suspension of ethyl 3-[2-chloro-5-(3,5-dimethyl-2,6-dioxo-4-thioxo-1,3,5-triazinan-1-yl)-4- fluoro-phenyl]-5-methyl-4H-isoxazole-5-carboxylate (400 mg, 0.87 mmol) in ethanol (5 ml) at room temperature. The resulting mixture was stirred for 30 mins, water (5 ml) added followed by dilute aqueous hydrochloric acid (2 ml). The mixture was filtered and the solid dried to provide 3-[2-chloro-4-fluoro-5-[[methyl(methylcarbamothioyl)carbamoyl]amino]phenyl]-5-methyl-4H-isoxazole-5-carboxylic acid as a white solid (260 mg).

$^1$H NMR (400 MHz, DMSO) δ 13.3 (br s, 1H), 10.15 (s, 2H), 7.95 (d, 1H), 7.7 (d, 1H), 3.85 (d, 1H), 3.55 (s, 3H), 3.4 (d, 1H), 3.0 (s, 3H), 1.6 (s, 3H) ppm.

Step 2 Preparation of 3-[2-chloro-5-(3,5-dimethyl-2, 6-dioxo-4-thioxo-1,3,5-triazinan-1-yl)-4-fluoro-phenyl]-5-methyl-4H-isoxazole-5-carboxylic Acid (compound 45)

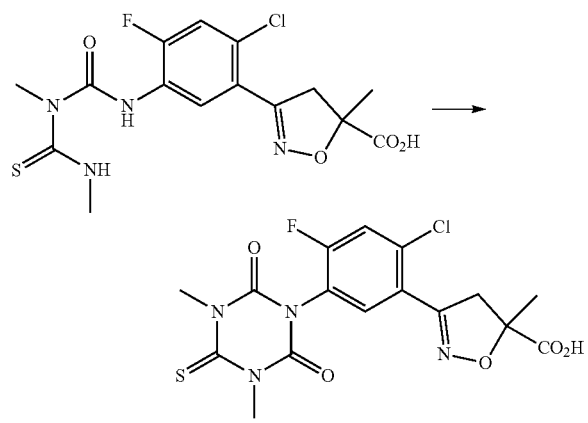

Triethylamine (0.068 ml, 0.48 mmol) followed by carbonyl di-imidazole (93 mg, 0.56 mmol) were added to a stirred solution of 3-[2-chloro-4-fluoro-5-[[methyl(methylcarbamothioyl)carbamoyl]amino]phenyl]-5-methyl-4H-isoxazole-5-carboxylic acid (150 mg, 0.37 mmol) in toluene (3 ml) at room temperature. The mixture was then heated at reflux for 3 hours, cooled and evaporated under reduced pressure to give a residue that was purified by chromatography to provide 3-[2-chloro-5-(3,5-dimethyl-2,6-dioxo-4-thioxo-1,3,5-triazinan-1-yl)-4-fluoro-phenyl]-5-methyl-4H-isoxazole-5-carboxylic acid (Compound 45) as a white solid (35 mg).

$^1$H NMR (400 MHz, CHCl$_3$) δ 7.7 (d, 1H), 7.3 (d, 1H), 5.2 (br s, 1H), 3.75 (d, 1H), 3.7 (s, 6H), 3.2 (d, 1H), 1.5 (s, 3H) ppm.

Example 3 Preparation of 3-[2,4-dichloro-5-(3,5-dimethyl-2,6-dioxo-4-thioxo-1,3,5-triazinan-1-yl)-phenyl]-5-methyl-4H-isoxazole-5-carboxylic Acid (Compound 56)

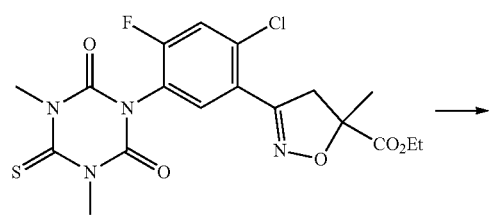

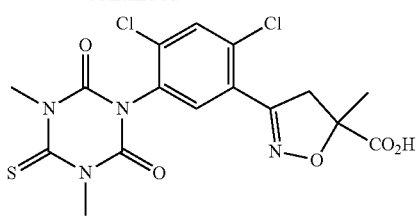

Concentrated sulfuric acid (0.75 ml, 13 mmol) was added to a stirred solution of ethyl 3-[2,4-dichloro-5-(3,5-dimethyl-2,6-dioxo-4-thioxo-1,3,5-triazinan-1-yl)phenyl]-5-methyl-4H-isoxazole-5-carboxylate (prepared as described in Example 1, Step 5; 300 mg, 0.63 mmol) in glacial acetic acid (3 ml) and the resulting mixture heated at 100° C. for 1 hour. The mixture was cooled to ambient temperature, poured into water and the resulting mixture extracted with dichloromethane. The organic extract was dried over magnesium sulfate, filtered and evaporated under reduced pressure to leave a residue that was purified by chromatography to provide 3-[2,4-dichloro-5-(3,5-dimethyl-2,6-dioxo-4-thioxo-1,3,5-triazinan-1-yl)-phenyl]-5-methyl-4H-isoxazole-5-carboxylic acid (Compound 56) as an oil (200 mg).

$^1$H NMR (400 MHz, CHCl$_3$) δ 7.75 (s, 1H), 7.65 (s, 1H), 5.75 (br s, 1H), 4.0 (d, 1H), 3.75 (s, 6H), 3.4 (d, 1H), 1.7 (s, 3H) ppm.

Example 4 Preparation of [3-(2-chloro-4-fluoro-5-nitro-phenyl)-5-methyl-4H-isoxazol-5-yl]methyl Acetate

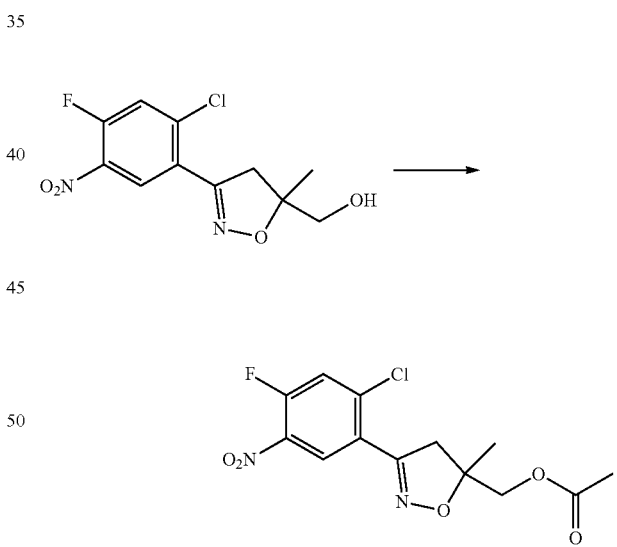

A mixture of [3-(2-chloro-4-fluoro-5-nitro-phenyl)-5-methyl-4H-isoxazol-5-yl]methanol (prepared as described in Example 1, Step 2; 150 mg, 0.52 mmol) and acetic anhydride (60 mg, 0.57 mmol) was heated at 90° C. for 2 hours, then allowed to cool and evaporated under reduced pressure to provide [3-(2-chloro-4-fluoro-5-nitro-phenyl)-5-methyl-4H-isoxazol-5-yl]methyl acetate as an oil (160 mg).

$^1$H NMR (400 MHz, CHCl$_3$) δ 8.45 (d, 1H), 7.45 (d, 1H), 4.3 (d, 1H), 4.15 (d, 1H), 3.5 (d, 1H), 3.25 (d, 1H), 2.1 (s, 3H), 1.5 (s, 3H) ppm.

Example 5 Preparation of 3-[4-chloro-2-fluoro-5-[5-(hydroxymethyl)-5-methyl-4H-isoxazol-3-yl]phenyl]-1,5-dimethyl-6-thioxo-1,3,5-triazinane-2,4-dione (Compound 49)

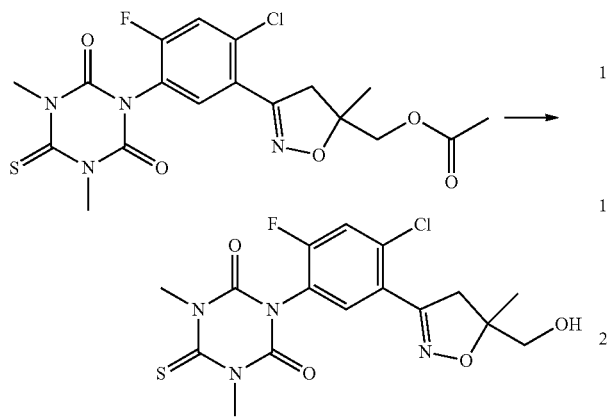

Saturated aqueous sodium hydrogen carbonate (76 mg, 0.89 mmol) was added to a stirred solution of [3-[2-chloro-5-(3,5-dimethyl-2,6-dioxo-4-thioxo-1,3,5-triazinan-1-yl)-4-fluoro-phenyl]-5-methyl-4H-isoxazol-5-yl]methyl acetate (prepared as described in Example 1, Step 5; 250 mg, 0.55 mmol) in methanol (25 ml). The mixture was stirred at room temperature for 17 hours, concentrated under reduced pressure and extracted with dichloromethane. The organic extracts were dried and evaporated under reduced pressure to leave a residue which was purified by chromatography to provide 3-[4-chloro-2-fluoro-5-[5-(hydroxymethyl)-5-methyl-4H-isoxazol-3-yl]phenyl]-1,5-dimethyl-6-thioxo-1,3,5-triazinane-2,4-dione (Compound 49) as a glassy solid (138 mg).

$^1$H NMR (400 MHz, CHCl$_3$) δ 7.75 (d, 1H), 7.55 (d, 1H), 3.75 (s, 6H), 3.65 (d, 1H), 3.55 (d, 1H), 3.3 (d, 1H), 3.2 (d, 1H), 1.45 (s, 3H) ppm (OH not observed).

Example 6 Preparation of [3-[2-chloro-5-(3,5-dimethyl-2,6-dioxo-4-thioxo-1,3,5-triazinan-1-yl)-4-fluoro-phenyl]-5-methyl-4H-isoxazol-5-yl]methyl Methanesulfonate (Compound 53)

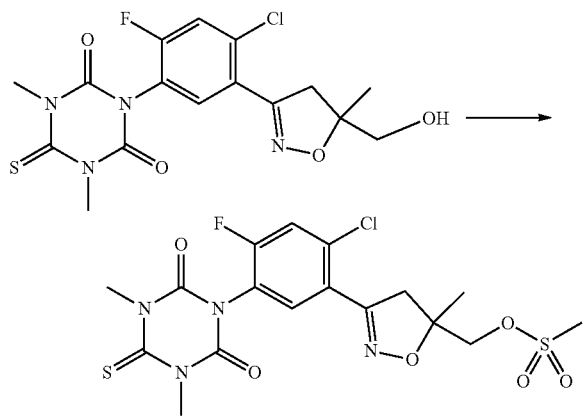

Methanesulfonyl chloride (0.1 ml, 1.0 mmol) was added to a stirred solution of 3-[4-chloro-2-fluoro-5-[5-(hydroxymethyl)-5-methyl-4H-isoxazol-3-yl]phenyl]-1,5-dimethyl-6-thioxo-1,3,5-triazinane-2,4-dione (prepared as described in Example 5; 38 mg, 0.077 mmol) in toluene (3 ml). The resulting solution was stirred at room temperature for 2 hours, evaporated under reduced pressure and the residue extracted with dichloromethane. The extracts were dried and evaporated under reduced pressure to leave a residue that was purified by chromatography to provide [3-[2-chloro-5-(3,5-dimethyl-2,6-dioxo-4-thioxo-1,3,5-triazinan-1-yl)-4-fluoro-phenyl]-5-methyl-4H-isoxazol-5-yl]methyl methanesulfonate (Compound 53) as a gum (40 mg).

$^1$H NMR (400 MHz, CHCl$_3$) δ 7.7 (d, 1H), 7.35 (d, 1H), 4.3 (q, 2H), 3.75 (s, 6H), 3.65 (d, 1H), 3.25 (d, 1H), 3.1 (s, 3H), 1.4 (s, 3H) ppm.

Example 7 Preparation of 3-[4-chloro-2-fluoro-5-[5-[N-methoxy-C-methyl-carbonimidoyl]-5-methyl-isoxazolidin-3-yl]phenyl]-1,5-dimethyl-6-thioxo-1,3,5-triazinane-2,4-dione (Compound 293)

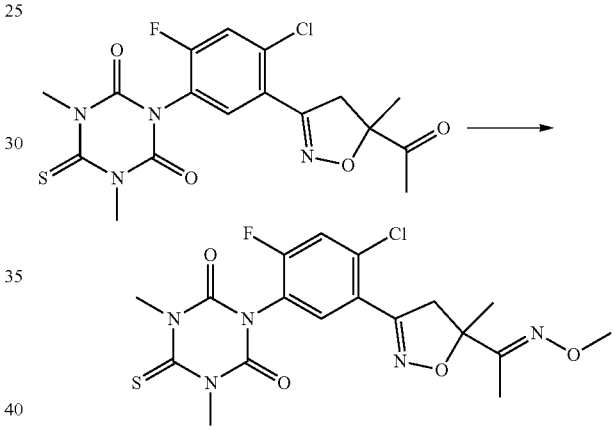

O-Methyl hydroxylamine hydrochloride (12 mg, 0.14 mmol) was added to a stirred solution of 3-[5-(5-acetyl-5-methyl-4H-isoxazol-3-yl)-4-chloro-2-fluoro-phenyl]-1,5-dimethyl-6-thioxo-1,3,5-triazinane-2,4-dione (prepared as described in Example 1, Step 5; 51 mg, 0.12 mmol) in ethanol (2.5 ml) and dichloromethane (2 ml). The resulting solution was stirred at room temperature for 17 hours, evaporated under reduced pressure and the residue partitioned between dichloromethane and water. The phases were separated and the organic dried and evaporated under reduced pressure to leave a residue that was purified by chromatography to provide 3-[4-chloro-2-fluoro-5-[5-[N-methoxy-C-methyl-carbonimidoyl]-5-methyl-isoxazolidin-3-yl]phenyl]-1,5-dimethyl-6-thioxo-1,3,5-triazinane-2,4-dione (Compound 293) as a fluffy solid (52 mg).

$^1$H NMR (400 MHz, CHCl$_3$) δ 7.7 (d, 1H), 7.35 (d, 1H), 4.1 (d, 1H), 3.85 (s, 3H), 3.8 (s, 6H), 3.2 (d, 1H), 1.95 (s, 3H), 1.6 (s, 3H) ppm.

Also prepared by this general method was:
3-[4-Chloro-2-fluoro-5-[5-[N-hydroxy-C-methyl-carbonimidoyl]-5-methyl-isoxazolidin-3-yl]phenyl]-1,5-dimethyl-6-thioxo-1,3,5-triazinane-2,4-dione (Compound 296)

$^1$H NMR (400 MHz, CHCl$_3$) δ 7.7 (d, 1H), 7.35 (d, 1H), 5.7 (br s, 1H), 3.9 (d, 1H), 3.75 (s, 6H), 3.3 (d, 1H), 2.0 (s, 3H), 1.65 (s, 3H) ppm.

Example 8 Preparation of Methyl 2-[1-[3-[2-chloro-5-(3,5-dimethyl-2,6-dioxo-4-thioxo-1,3,5-triazinan-1-yl)-4-fluoro-phenyl]-5-methyl-4H-isoxazol-5-yl]ethylideneamino]oxyacetate (Compound 299)

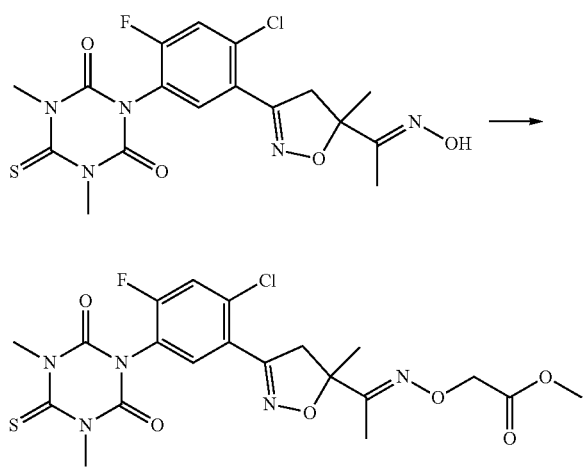

Methyl bromoacetate (0.01 ml, 0.1 mmol), followed by potassium carbonate (12.5 mg, 0.09 mmol) and potassium iodide (catalytic), were added to a solution of 3-[4-chloro-2-fluoro-5-[5-[N-hydroxy-C-methyl-carbonimidoyl]-5-methyl-isoxazolidin-3-yl]phenyl]-1,5-dimethyl-6-thioxo-1,3,5-triazinane-2,4-dione (prepared as described in Example 7; 40 mg, 0.09 mmol) in 4-methyl pentan-2-one (2 ml). The resulting mixture was heated in a microwave oven for 1 hour at 100° C., allowed to cool and the solvent evaporated under reduced pressure to leave a solid that was purified by chromatography to provide methyl 2-[1-[3-[2-chloro-5-(3,5-dimethyl-2,6-dioxo-4-thioxo-1,3,5-triazinan-1-yl)-4-fluoro-phenyl]-5-methyl-4H-isoxazol-5-yl]ethylideneamino]oxyacetate (Compound 299) as a gum (20 mg).

$^1$H NMR (400 MHz, CHCl$_3$) δ 7.7 (d, 1H), 7.35 (d, 1H), 4.6 (s, 2H), 4.0 (d, 1H), 3.8 (s, 6H), 3.7 (s, 3H), 3.2 (d, 1H), 2.0 (s, 3H), 1.6 (s, 3H) ppm.

Example 9 Preparation of 3-[2-chloro-5-(3,5-dimethyl-2,6-dioxo-4-thioxo-1,3,5-triazinan-1-yl)-4-fluoro-phenyl]-5-methyl-4H-isoxazole-5-carboxamide (Compound 308)

Step 1 Preparation of 3-[2-chloro-5-(3,5-dimethyl-2,6-dioxo-4-thioxo-1,3,5-triazinan-1-yl)-4-fluoro-phenyl]-5-methyl-4H-isoxazole-5-carbonyl Chloride

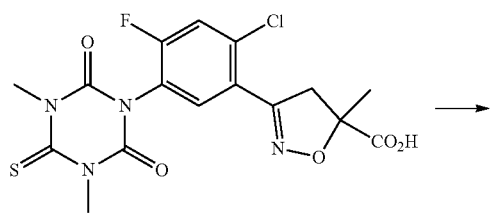

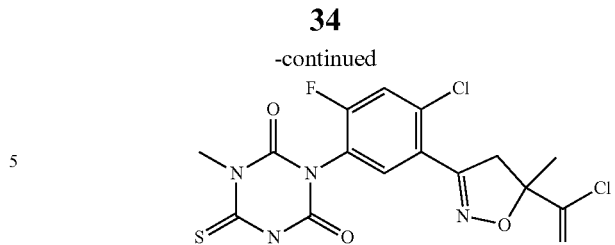

Oxalyl chloride (0.01 ml, 0.11 mmol) followed by dimethylformamide (drop) were added to a stirred solution of 3-[2-chloro-5-(3,5-dimethyl-2,6-dioxo-4-thioxo-1,3,5-triazinan-1-yl)-4-fluoro-phenyl]-5-methyl-4H-isoxazole-5-carboxylic acid (prepared as described in example 3; 42 mg, 0.10 mmol) in dichloromethane (2 ml) at 0° C. The resulting solution was stirred for 5 minutes, then allowed to warm to ambient temperature and used directly.

Step 2 Preparation of 3-[2-chloro-5-(3,5-dimethyl-2,6-dioxo-4-thioxo-1,3,5-triazinan-1-yl)-4-fluoro-phenyl]-5-methyl-4H-isoxazole-5-carboxamide (Compound 308)

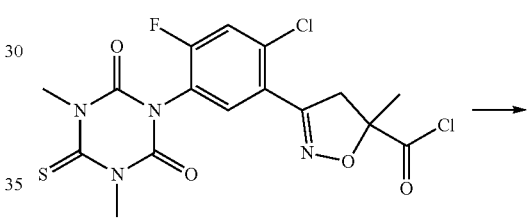

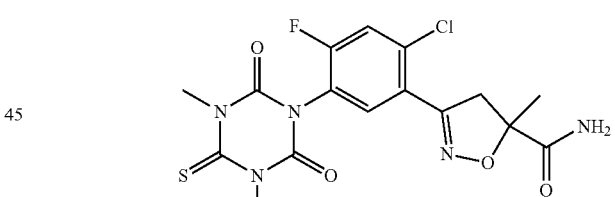

Concentrated aqueous ammonia (0.5 ml, 30 mmol) was added to the stirred solution of 3-[2-chloro-5-(3,5-dimethyl-2,6-dioxo-4-thioxo-1,3,5-triazinan-1-yl)-4-fluoro-phenyl]-5-methyl-4H-isoxazole-5-carbonyl chloride in dichloromethane (2 ml) at 0° C. The resulting solution was stirred for 30 minutes then evaporated under reduced pressure to leave a white solid which was triturated with water to provide 3-[2-chloro-5-(3,5-dimethyl-2,6-dioxo-4-thioxo-1,3,5-triazinan-1-yl)-4-fluoro-phenyl]-5-methyl-4H-isoxazole-5-carboxamide (Compound 308) as a white solid (35 mg).

$^1$H NMR (400 MHz, d6-DMSO) δ 7.9 (m, 2H), 7.6 (br s, 1H), 7.4 (br s, 1H), 3.8 (d, 1H), 3.65 (s, 6H), 1.6 (s, 3H) ppm (1 CH not observed due to water suppression).

Example 10 Preparation of 3-[2-chloro-5-(3,5-dimethyl-2,6-dioxo-4-thioxo-1,3,5-triazinan-1-yl)-4-fluoro-phenyl]-5-methyl-N-methylsulfonyl-4H-isoxazole-5-carboxamide (Compound 284)

Step 1 Preparation of 3-[4-chloro-2-fluoro-5-[5-(imidazole-1-carbonyl)-5-methyl-4H-isoxazol-3-yl]phenyl]-1,5-dimethyl-6-thioxo-1,3,5-triazinane-2,4-dione

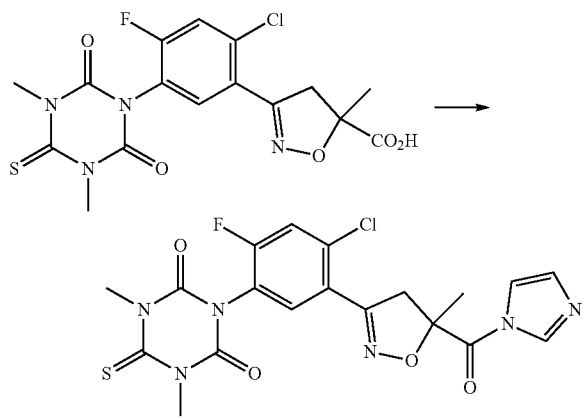

Carbonyl diimidazole (234 mg, 1.4 mmol) was added to a stirred solution of 3-[2-chloro-5-(3,5-dimethyl-2,6-dioxo-4-thioxo-1,3,5-triazinan-1-yl)-4-fluoro-phenyl]-5-methyl-4H-isoxazole-5-carboxylic acid (prepared as described in example 3; 400 mg, 0.93 mmol) and triethylamine (0.17 ml, 0.93 mmol) in dichloromethane (5 ml) at ambient temperature. The resulting solution was stirred for 45 minutes, then the solvent evaporated under reduced pressure to provide 3-[4-chloro-2-fluoro-5-[5-(imidazole-1-carbonyl)-5-methyl-4H-isoxazol-3-yl]phenyl]-1,5-dimethyl-6-thioxo-1,3,5-triazinane-2,4-dione which was used directly.

Step 2 Preparation of 3-[2-chloro-5-(3,5-dimethyl-2,6-dioxo-4-thioxo-1,3,5-triazinan-1-yl)-4-fluoro-phenyl]-5-methyl-N-methylsulfonyl-4H-isoxazole-5-carboxamide (Compound 284)

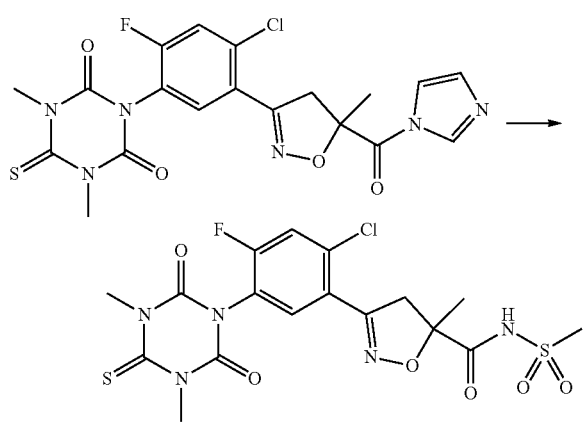

DBU (0.13 ml, 0.84 mmol) was added to the stirred solution of 3-[4-chloro-2-fluoro-5-[5-(imidazole-1-carbonyl)-5-methyl-4H-isoxazol-3-yl]phenyl]-1,5-dimethyl-6-thioxo-1,3,5-triazinane-2,4-dione (200 mg, 0.42 mmol) and methanesulfonamide (82 mg, 0.84 mmol) in dichloromethane (5 ml) at ambient temperature. The resulting solution was stirred for 40 hours then evaporated under reduced pressure to leave a yellow oil which was purified by chromatography to provide 3-[2-chloro-5-(3,5-dimethyl-2,6-dioxo-4-thioxo-1,3,5-triazinan-1-yl)-4-fluoro-phenyl]-5-methyl-N-methylsulfonyl-4H-isoxazole-5-carboxamide (Compound 284) as a white solid (52 mg).

$^1$H NMR (400 MHz, CHCl$_3$) δ 9.1 (br s, 1H), 7.7 (d, 1H), 7.4 (d, 1H), 4.0 (d, 1H), 3.75 (s, 6H), 3.45 (d, 1H), 3.3 (s, 3H), 1.75 (s, 3H) ppm.

Also prepared by this general method was:
3-[2-Chloro-5-(3,5-dimethyl-2,6-dioxo-4-thioxo-1,3,5-triazinan-1-yl)-4-fluoro-phenyl]-N-(dimethylsulfamoyl)-5-methyl-4H-isoxazole-5-carboxamide (Compound 305)

$^1$H NMR (400 MHz, CHCl$_3$) δ 8.95 (brs, 1H), 7.7 (d, 1H), 7.4 (d, 1H), 4.0 (d, 1H), 3.75 (s, 6H), 3.45 (d, 1H), 2.95 (s, 6H), 1.75 (s, 3H) ppm.

FORMULATION EXAMPLES

| Wettable powders | | | |
|---|---|---|---|
|  | a) | b) | c) |
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | | | |
|---|---|---|---|
|  | a) | b) | c) |
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

BIOLOGICAL EXAMPLES

Pre-Emergence Biological Efficacy

Seeds of weeds and/or crops were sown in standard soil in pots. After cultivation for one day under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethylene sorbitan monolaurate, CAS RN 9005-64-5) to give the desired final dose of test compound.

The test plants were then grown under controlled conditions in the glasshouse (at 24/16° C., day/night; 14 hours light; 65% humidity) and watered twice daily. After 13 days the test was evaluated (100=total damage to plant; 0=no damage to plant). The results are shown in Table 2 below.

TABLE 2

| Compound | Rate (g/ha) | Species | | | | | |
|---|---|---|---|---|---|---|---|
| | | AMAPA | LOLPE | EPHHL | SETFA | ECHCG | IPOHE |
| 36 | 250 | 70 | 10 | 70 | 90 | 90 | 40 |
| 45 | 250 | 100 | 100 | 100 | 100 | 100 | 100 |
| 47 | 250 | 100 | 70 | 100 | 100 | 100 | 100 |
| 47 (enantiomer A) | 250 | 100 | 50 | 100 | 100 | 60 | 90 |
| 47 (enantiomer B) | 250 | 100 | 40 | 100 | 100 | 50 | 80 |
| 49 | 250 | 100 | 90 | 100 | 100 | 90 | 90 |
| 51 | 250 | 100 | 90 | 100 | 100 | 90 | 80 |
| 53 | 250 | 100 | 70 | — | 100 | 60 | 0 |
| 56 | 250 | 90 | 10 | 10 | 10 | 0 | 30 |
| 58 | 250 | 90 | 0 | 0 | 0 | 0 | 60 |
| 145 | 250 | 100 | 90 | 100 | 100 | 90 | 100 |
| 262 | 250 | — | 30 | 0 | 50 | 30 | 0 |
| 284 | 250 | 100 | 40 | 100 | 70 | 30 | 100 |
| 290 | 250 | 100 | 90 | 100 | 100 | 90 | 100 |
| 293 | 250 | 100 | 90 | 100 | 100 | 90 | 50 |
| 296 | 250 | 100 | 80 | 90 | 100 | 80 | 90 |
| 299 | 250 | 100 | 60 | 90 | 60 | 0 | 80 |
| 305 | 250 | 100 | 30 | 60 | 90 | 30 | 80 |
| 308 | 250 | 100 | 60 | 80 | 90 | 10 | 50 |
| 311 | 250 | 100 | 10 | 50 | 90 | 10 | 70 |

Post-Emergence Biological Efficacy

Seeds of weeds and/or crops were sown in standard soil in pots. After cultivation for 8 days under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethylene sorbitan monolaurate, CAS RN 9005-64-5) to give the desired final dose of test compound.

The test plants were then grown on under controlled conditions in a glasshouse (at 24/16° C., day/night; 14 hours light; 65% humidity) and watered twice daily. After 13 days the test was evaluated (100=total damage to plant; 0=no damage to plant). The results are shown in Table 3 below.

TABLE 3

| Compound | Rate (g/ha) | AMAPA | CHEAL | EPHHL | IPOHE | ELEIN | LOLPE | DIGSA | SETFA | ECHCG |
|---|---|---|---|---|---|---|---|---|---|---|
| 36 | 250 | 100 | 90 | 90 | 70 | 50 | 50 | 100 | 100 | 100 |
| 45 | 250 | 100 | 100 | 100 | 100 | 100 | 100 | 100 | 100 | 100 |
| 47 | 250 | 100 | 100 | 100 | 100 | 100 | 100 | 100 | 100 | 100 |
| 47 (enantiomer A) | 250 | 100 | 100 | 90 | 100 | 90 | 70 | 100 | 100 | 100 |
| 47 (enantiomer B) | 250 | 100 | 100 | 100 | 100 | 100 | 100 | 100 | 100 | 100 |
| 49 | 250 | 100 | 100 | 100 | 100 | 90 | 60 | 90 | 100 | 70 |
| 51 | 250 | 100 | 100 | 100 | 90 | 80 | 50 | 100 | 100 | 30 |
| 53 | 250 | 90 | 90 | 90 | 80 | 80 | 40 | 70 | 40 | 30 |
| 56 | 250 | 100 | 90 | 80 | 90 | 80 | 30 | 80 | 90 | 90 |
| 58 | 250 | 90 | 90 | 70 | 100 | 90 | 30 | 80 | 90 | 90 |
| 145 | 250 | 100 | 100 | 100 | 100 | 100 | 100 | 100 | 100 | 100 |
| 262 | 250 | 40 | 30 | 60 | 50 | 40 | 0 | 50 | 30 | 20 |
| 284 | 250 | 100 | 100 | 90 | 100 | 100 | 80 | 100 | 100 | 100 |
| 290 | 250 | 100 | 100 | 100 | 100 | 100 | 90 | 100 | 90 | 90 |
| 293 | 250 | 100 | 100 | 100 | 100 | 90 | 60 | 100 | 90 | 30 |
| 296 | 250 | 100 | 100 | 80 | 90 | 90 | 70 | 70 | 80 | 30 |
| 299 | 250 | 100 | 100 | 90 | 90 | 90 | 90 | 80 | 100 | 100 |
| 305 | 250 | 100 | 100 | 100 | 100 | 100 | 100 | 100 | 100 | 100 |
| 308 | 250 | 100 | 100 | 90 | 100 | 100 | 90 | 100 | 100 | 100 |
| 311 | 250 | 90 | 90 | 90 | 90 | 90 | 50 | 80 | 100 | 90 |

The invention claimed is:

1. A compound of formula (I) or an agronomically acceptable salt thereof:

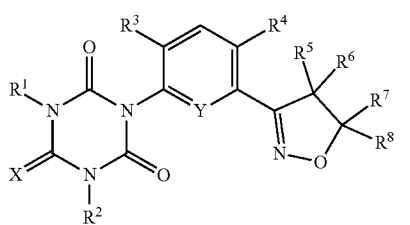

wherein

X is selected from the group consisting of oxygen and sulfur;

Y is selected from the group consisting of C—H and nitrogen;

$R^1$ is selected from the group consisting of hydrogen and $C_1$-$C_6$alkyl;

$R^2$ is selected from the group consisting of hydrogen, amino, $C_1$-$C_6$alkyl, $C_3$-$C_6$alkenyl and $C_3$-$C_6$alkynyl;

$R^3$ is selected from the group consisting of hydrogen, halogen, $C_1$-$C_4$alkyl, $C_1$-$C_4$haloalkyl, $C_1$-$C_4$alkoxy, $C_1$-$C_4$haloalkoxy and $C_1$-$C_4$alkylsulfonyl;

$R^4$ is selected from the group consisting of hydrogen, halogen, cyano, aminocarbonyl, aminothiocarbonyl, $C_1$-$C_4$alkyl, $C_1$-$C_4$haloalkyl, $C_1$-$C_4$alkoxy, $C_1$-$C_4$haloalkoxy and $C_1$-$C_4$alkylsulfonyl;

each $R^5$ and $R^6$ is independently selected from the group consisting of hydrogen, cyano, $C_1$-$C_6$alkyl, $C_1$-$C_6$haloalkyl, $C_1$-$C_4$alkylsulfonyl, $CO_2R^9$, $CONR^{10}R^{11}$ and $CH_2OR^{12}$;

each $R^7$ and $R^8$ is independently selected from the group consisting of hydrogen, cyano, $C_1$-$C_6$alkyl, $C_1$-$C_6$haloalkyl, $C_1$-$C_4$alkoxy, $C_1$-$C_4$alkylsulfonyl, $C(=Z)R^{15}$, $CO_2R^9$, $CONR^{10}R^{11}$ and $CH_2OR^{12}$;

Z is selected from the group consisting of oxygen, $NOR^{16}$ and $NN(R^{16})_2$;

$R^9$ is selected from the group consisting of hydrogen, $C_1$-$C_{10}$alkyl, $C_1$-$C_{10}$haloalkyl, $C_3$-$C_6$alkenyl, $C_3$-$C_6$haloalkenyl, $C_3$-$C_6$alkynyl, $C_1$-$C_4$alkoxy$C_1$-$C_6$alkyl, $C_1$-$C_4$haloalkoxy$C_1$-$C_6$alkyl, $C_6$-$C_{10}$aryl$C_1$-$C_3$alkyl, $C_6$-$C_{10}$aryl$C_1$-$C_3$alkyl substituted by 1-4 groups $R^{13}$, heteroaryl$C_1$-$C_3$alkyl and heteroaryl$C_1$-$C_3$alkyl substituted by 1-3 groups $R^{13}$;

$R^{10}$ is selected from the group consisting of hydrogen, $C_1$-$C_6$alkyl and $SO_2R^{14}$;

$R^{11}$ is selected from the group consisting of hydrogen and $C_1$-$C_6$alkyl; or $R^{10}$ and $R^{11}$ together with the nitrogen to which they are attached form a 3- to 6-membered heterocyclyl ring, which optionally contains an oxygen atom;

$R^{12}$ is selected from the group consisting of hydrogen, $C_1$-$C_4$alkyl, $C_1$-$C_4$haloalkyl, $C_1$-$C_4$alkylsulfonyl, $C_1$-$C_4$haloalkylsulfonyl, phenylsulphonyl, phenylsulfonyl substituted by 1-2 groups $R^{13}$; $C_1$-$C_4$alkylcarbonyl, $C_1$-$C_4$haloalkylcarbonyl, $C_6$-$C_{10}$arylcarbonyl, $C_6$-$C_{10}$arylcarbonyl substituted by 1-4 groups $R^{13}$, heteroarylcarbonyl, heteroarylcarbonyl substituted by 1-3 groups $R^{13}$, $C_6$-$C_{10}$aryl$C_1$-$C_3$alkylcarbonyl, $C_6$-$C_{10}$aryl$C_1$-$C_3$alkylcarbonyl substituted by 1-4 groups $R^{13}$, heteroaryl$C_1$-$C_3$alkylcarbonyl and heteroaryl$C_1$-$C_3$alkylcarbonyl substituted by 1-3 groups $R^{13}$;

each $R^{13}$ is independently selected from the group consisting of halogen, $C_1$-$C_4$alkyl, $C_1$-$C_4$haloalkyl, $C_1$-$C_4$alkoxy, $C_1$-$C_4$haloalkoxy, cyano and $C_1$-$C_4$alkylsulfonyl;

$R^{14}$ is selected from the group consisting of $C_1$-$C_4$alkyl, $C_1$-$C_4$haloalkyl, and $C_1$-$C_4$alkyl($C_1$-$C_4$alkyl)amino;

$R^{15}$ is selected from the group consisting of hydrogen, $C_1$-$C_4$alkyl and $C_1$-$C_4$haloalkyl;

$R^{16}$ is selected from the group consisting of hydrogen, $C_1$-$C_4$alkyl, $C_1$-$C_4$haloalkyl and $C_1$-$C_4$alkoxycarbonyl$C_1$-$C_4$alkyl.

2. A compound as claimed in claim 1 in which X is sulfur.

3. A compound as claimed in claim 1 in which Y is C—H.

4. A compound as claimed in claim 1 in which $R^1$ is selected from the group consisting of hydrogen and $C_1$-$C_4$alkyl.

5. A compound as claimed in claim 1 in which $R^2$ is selected from the group consisting of hydrogen, $C_1$-$C_4$alkyl and $C_3$-$C_4$alkynyl.

6. A compound as claimed in claim 1 in which $R^3$ is selected from the group consisting of hydrogen, chlorine and fluorine.

7. A compound as claimed in claim 1 in which $R^4$ is selected from the group consisting of hydrogen, chlorine, cyano and aminothiocarbonyl.

8. A compound as claimed in claim 1 in which each $R^5$ and $R^6$ is independently selected from the group consisting of hydrogen, $C_1$-$C_4$alkyl, $CO_2R^9$ and $CH_2OR^{12}$.

9. A compound as claimed in claim 1 in which each $R^7$ and $R^8$ is independently selected from the group consisting of hydrogen, $C_1$-$C_4$alkyl, $C_1$-$C_6$haloalkyl, $CO_2R^9$, $CONR^{10}R^{11}$ and $CH_2OR^{12}$.

10. A compound as claimed in claim 1 in which $R^9$ is selected from the group consisting of hydrogen, $C_1$-$C_4$alkyl, $C_1$-$C_4$haloalkyl, $C_1$-$C_2$alkoxy$C_1$-$C_2$alkyl, phenyl$C_1$-$C_2$alkyl and phenyl$C_1$-$C_2$alkyl substituted by 1-2 groups $R^{13}$.

11. A compound as claimed in claim 1 in which $R^{10}$ is selected from the group consisting of hydrogen and $SO_2R^{14}$.

12. A compound as claimed in claim 1 in which $R^{11}$ is hydrogen.

13. A compound as claimed in claim 1 in which $R^{12}$ is selected from the group consisting of hydrogen, $C_1$-$C_2$alkyl, $C_1$-$C_2$alkylsulfonyl, $C_1$-$C_2$haloalkylsulfonyl, $C_1$-$C_4$alkylcarbonyl, phenylcarbonyl, phenylcarbonyl substituted by 1-2 groups $R^{13}$, phenyl$C_1$-$C_2$alkylcarbonyl and phenyl$C_1$-$C_2$alkylcarbonyl substituted by 1-2 groups $R^{13}$.

14. A compound as claimed in claim 1 in which $R^{13}$ is selected from the group consisting of halogen, $C_1$-$C_4$alkyl, $C_1$-$C_4$haloalkyl, $C_1$-$C_4$alkoxy, $C_1$-$C_4$haloalkoxy, cyano and $C_1$-$C_4$alkylsulfonyl.

15. A compound as claimed in claim 1 in which $R^{14}$ is selected from the group consisting of $C_1$-$C_4$alkyl and $C_1$-$C_4$alkyl($C_1$-$C_4$alkyl)amino.

16. An agrochemical composition comprising a herbicidally effective amount of a compound of formula (I) as defined in claim 1 and an agrochemically-acceptable diluent or carrier.

17. A method of controlling or preventing undesirable plant growth, wherein a herbicidally effective amount of a compound of formula (I) as defined in claim 1 is applied to the plants, to parts thereof or to the locus thereof.

18. A compound as claimed in claim 2 in which Y is C—H.

19. A method of controlling or preventing undesirable plant growth, wherein a herbicidally effective amount of a compound of formula (I) as defined in a composition according to claim 16, is applied to the plants, to parts thereof or to the locus thereof.

* * * * *